(12) United States Patent
LeBoeuf et al.

(10) Patent No.: US 10,092,245 B2
(45) Date of Patent: Oct. 9, 2018

(54) METHODS AND APPARATUS FOR DETECTING MOTION NOISE AND FOR REMOVING MOTION NOISE FROM PHYSIOLOGICAL SIGNALS

(71) Applicant: Valencell, Inc., Raleigh, NC (US)

(72) Inventors: Steven Francis LeBoeuf, Raleigh, NC (US); Jesse Berkley Tucker, Youngsville, NC (US); Michael Edward Aumer, Raleigh, NC (US)

(73) Assignee: Valencell, Inc., Raleigh, NC (US)

( * ) Notice: Subject to any disclaimer, the term of this patent is extended or adjusted under 35 U.S.C. 154(b) by 640 days.

(21) Appl. No.: 14/740,804

(22) Filed: Jun. 16, 2015

(65) Prior Publication Data

US 2015/0289818 A1    Oct. 15, 2015

Related U.S. Application Data

(60) Continuation of application No. 14/159,156, filed on Jan. 20, 2014, which is a division of application No.
(Continued)

(51) Int. Cl.
*A61B 5/1455* (2006.01)
*A61B 5/00* (2006.01)
(Continued)

(52) U.S. Cl.
CPC .............. *A61B 5/7221* (2013.01); *A61B 5/00* (2013.01); *A61B 5/002* (2013.01); *A61B 5/0013* (2013.01);
(Continued)

(58) Field of Classification Search
CPC .............. A61B 5/1455; A61B 5/14551; A61B 5/14552; A61B 5/14532; A61B 5/72;
(Continued)

(56) References Cited

U.S. PATENT DOCUMENTS

| 3,595,219 A | 7/1971 | Friedlander et al. |
| 3,638,640 A * | 2/1972 | Shaw ............... A61B 5/14552 356/41 |

(Continued)

FOREIGN PATENT DOCUMENTS

| CA | 2 875 901 A1 | 12/2012 |
| CN | 101212927 A | 7/2008 |

(Continued)

OTHER PUBLICATIONS

Han et al., "Artifacts in wearable photoplethysmographs during daily life motions and their reduction with least mean square based active noise cancellation method," Computers in Biology and Medicine, 42, 2012, pp. 387-393.
(Continued)

*Primary Examiner* — Eric Winakur
*Assistant Examiner* — Chu Chuan (JJ) Liu
(74) *Attorney, Agent, or Firm* — Myers Bigel, P.A.

(57) ABSTRACT

Methods and apparatus are presented for removing motion artifacts from physiological signals produced by a physiological sensor of a wearable device, wherein the physiological sensor includes at least one optical emitter and at least one optical detector. Light emitted by the at least one optical emitter that is scattered by a body of a subject wearing the device is detected, and a physiological information signal therefrom is produced via the at least one optical detector. Light emitted by the at least one optical emitter that is scattered by a light regulating region of the wearable device is detected, and a motion noise information signal is produced via the at least one optical detector. The physiological information signal and the motion noise information signal are processed via at least one processor associated with the wearable device to at least partially
(Continued)

remove unwanted motion artifacts from the physiological information signal.

25 Claims, 8 Drawing Sheets

Related U.S. Application Data

12/692,807, filed on Jan. 25, 2010, now Pat. No. 8,647,270.

(60) Provisional application No. 61/208,567, filed on Feb. 25, 2009, provisional application No. 61/208,574, filed on Feb. 25, 2009, provisional application No. 61/212,444, filed on Apr. 13, 2009, provisional application No. 61/274,191, filed on Aug. 14, 2009.

(51) Int. Cl.

| | | |
|---|---|---|
| *G06F 19/00* | (2018.01) | |
| *A61B 5/024* | (2006.01) | |
| *H04R 1/10* | (2006.01) | |
| *A61B 5/0205* | (2006.01) | |
| *A61B 5/11* | (2006.01) | |
| *A61B 5/0476* | (2006.01) | |
| *A61B 5/16* | (2006.01) | |
| *F21V 8/00* | (2006.01) | |
| *A61B 5/021* | (2006.01) | |
| *A61B 5/08* | (2006.01) | |
| *A61B 5/01* | (2006.01) | |
| *A61B 5/145* | (2006.01) | |
| *H04R 1/02* | (2006.01) | |
| *A61B 5/026* | (2006.01) | |
| *A61B 5/0295* | (2006.01) | |
| *A61B 5/091* | (2006.01) | |

(52) U.S. Cl.
CPC .......... *A61B 5/0022* (2013.01); *A61B 5/0024* (2013.01); *A61B 5/0059* (2013.01); *A61B 5/0082* (2013.01); *A61B 5/0084* (2013.01); *A61B 5/01* (2013.01); *A61B 5/021* (2013.01); *A61B 5/0205* (2013.01); *A61B 5/02055* (2013.01); *A61B 5/0261* (2013.01); *A61B 5/02427* (2013.01); *A61B 5/02433* (2013.01); *A61B 5/0476* (2013.01); *A61B 5/0816* (2013.01); *A61B 5/11* (2013.01); *A61B 5/1107* (2013.01); *A61B 5/1118* (2013.01); *A61B 5/1455* (2013.01); *A61B 5/14532* (2013.01); *A61B 5/14551* (2013.01); *A61B 5/165* (2013.01); *A61B 5/418* (2013.01); *A61B 5/486* (2013.01); *A61B 5/4812* (2013.01); *A61B 5/4845* (2013.01); *A61B 5/4848* (2013.01); *A61B 5/4866* (2013.01); *A61B 5/4875* (2013.01); *A61B 5/4884* (2013.01); *A61B 5/6803* (2013.01); *A61B 5/6815* (2013.01); *A61B 5/6816* (2013.01); *A61B 5/6817* (2013.01); *A61B 5/6819* (2013.01); *A61B 5/6826* (2013.01); *A61B 5/6838* (2013.01); *A61B 5/721* (2013.01); *A61B 5/725* (2013.01); *A61B 5/7214* (2013.01); *A61B 5/7278* (2013.01); *A61B 5/7282* (2013.01); *A61B 5/742* (2013.01); *A61B 5/7475* (2013.01); *G02B 6/0001* (2013.01); *G06F 19/00* (2013.01); *G06F 19/3418* (2013.01); *H04R 1/028* (2013.01); *H04R 1/105* (2013.01); *H04R 1/1091* (2013.01); *A61B 5/024* (2013.01); *A61B 5/026* (2013.01); *A61B 5/0295* (2013.01); *A61B 5/02405* (2013.01); *A61B 5/02416* (2013.01); *A61B 5/091* (2013.01); *A61B 5/411* (2013.01); *A61B 5/415* (2013.01); *A61B 5/7207* (2013.01); *A61B 2560/0242* (2013.01); *A61B 2560/0425* (2013.01); *A61B 2560/0443* (2013.01); *A61B 2562/0219* (2013.01); *A61B 2562/0233* (2013.01); *Y02A 90/26* (2018.01)

(58) Field of Classification Search
CPC ..... A61B 5/6814; A61B 5/6815; A61B 5/021; A61B 5/02433; A61B 5/0261; A61B 5/0816; A61B 5/165; A61B 5/4845; A61B 5/4875
See application file for complete search history.

(56) References Cited

U.S. PATENT DOCUMENTS

| | | | |
|---|---|---|---|
| 4,240,882 A | 12/1980 | Ang et al. | |
| 4,331,154 A | 5/1982 | Broadwater et al. | |
| 4,438,772 A | 3/1984 | Slavin | |
| 4,491,760 A | 1/1985 | Linvill | |
| 4,521,499 A | 6/1985 | Switzer | |
| 4,541,905 A | 9/1985 | Kuwana et al. | |
| 4,592,807 A | 6/1986 | Switzer | |
| 4,655,225 A | 4/1987 | Dahne et al. | |
| 4,830,014 A | 5/1989 | Goodman et al. | |
| 4,882,492 A | 11/1989 | Schlager | |
| 4,896,676 A | 1/1990 | Sasaki | |
| 4,928,704 A | 5/1990 | Hardt | |
| 4,952,890 A | 8/1990 | Swanson | |
| 4,952,928 A | 8/1990 | Carroll et al. | |
| 4,957,109 A | 9/1990 | Groeger et al. | |
| 5,002,060 A | 3/1991 | Nedivi | |
| 5,022,970 A | 6/1991 | Cook et al. | |
| 5,025,791 A * | 6/1991 | Niwa | A61B 5/14552 600/324 |
| 5,063,781 A * | 11/1991 | Conforti | G01H 9/006 250/227.29 |
| 5,079,421 A | 1/1992 | Knudson et al. | |
| 5,080,098 A | 1/1992 | Willett et al. | |
| 5,086,229 A | 2/1992 | Rosenthal et al. | |
| 5,139,025 A | 8/1992 | Lewis et al. | |
| 5,143,078 A | 9/1992 | Mather et al. | |
| 5,226,417 A | 7/1993 | Swedlow et al. | |
| 5,237,994 A | 8/1993 | Goldberger | |
| 5,237,997 A | 8/1993 | Greubel et al. | |
| 5,299,570 A | 4/1994 | Hatschek | |
| 5,348,002 A | 9/1994 | Caro | |
| 5,377,100 A | 12/1994 | Pope et al. | |
| 5,431,170 A * | 7/1995 | Mathews | A61B 5/0002 600/323 |
| 5,448,082 A | 9/1995 | Kim | |
| 5,482,036 A | 1/1996 | Diab et al. | |
| 5,492,129 A | 2/1996 | Greenberger | |
| 5,494,043 A | 2/1996 | O'Sullivan et al. | |
| 5,499,301 A | 3/1996 | Sudo et al. | |
| 5,581,648 A | 12/1996 | Sahagen | |
| 5,596,987 A | 1/1997 | Chance | |
| 5,611,337 A | 3/1997 | Bukta | |
| 5,662,117 A | 9/1997 | Bittman | |
| 5,666,952 A | 9/1997 | Fuse et al. | |
| 5,673,692 A | 10/1997 | Schulze et al. | |
| 5,697,374 A | 12/1997 | Odagiri et al. | |
| 5,705,809 A * | 1/1998 | Kershaw | G01D 5/30 250/227.14 |
| 5,711,308 A | 1/1998 | Singer | |
| 5,725,480 A | 3/1998 | Oosta et al. | |
| 5,743,260 A | 4/1998 | Chung et al. | |
| 5,779,631 A | 7/1998 | Chance | |
| 5,797,841 A | 8/1998 | Delonzor et al. | |
| 5,807,114 A | 9/1998 | Hodges et al. | |
| 5,807,267 A | 9/1998 | Bryars et al. | |
| 5,817,008 A | 10/1998 | Rafert et al. | |

(56) References Cited

U.S. PATENT DOCUMENTS

| | | |
|---|---|---|
| 5,846,190 A | 12/1998 | Woehrle |
| 5,853,005 A | 12/1998 | Scanlon |
| 5,904,654 A | 5/1999 | Wohltmann et al. |
| 5,938,593 A | 8/1999 | Quellette |
| 5,954,644 A | 9/1999 | Dettling et al. |
| 5,964,701 A | 10/1999 | Asada et al. |
| 5,971,931 A | 10/1999 | Raff |
| 5,974,338 A | 10/1999 | Asano et al. |
| 5,995,858 A | 11/1999 | Kinast |
| 6,004,274 A | 12/1999 | Aceti et al. |
| 6,013,007 A | 1/2000 | Root et al. |
| 6,022,748 A | 2/2000 | Charych et al. |
| 6,023,541 A | 2/2000 | Merchant et al. |
| 6,030,342 A | 2/2000 | Amano et al. |
| 6,045,511 A | 4/2000 | Ott et al. |
| 6,067,006 A | 5/2000 | O'Brien |
| 6,070,093 A | 5/2000 | Oosta et al. |
| 6,078,829 A | 6/2000 | Uchida et al. |
| 6,080,110 A | 6/2000 | Thorgersen |
| 6,081,742 A | 6/2000 | Amano et al. |
| 6,125,291 A | 9/2000 | Miesel et al. |
| 6,134,458 A | 10/2000 | Rosenthal |
| 6,155,983 A | 12/2000 | Kosuda et al. |
| 6,168,567 B1 | 1/2001 | Pickering et al. |
| 6,186,145 B1 | 2/2001 | Brown |
| 6,198,394 B1 | 3/2001 | Jacobsen et al. |
| 6,198,951 B1 | 3/2001 | Kosuda et al. |
| 6,205,354 B1 | 3/2001 | Gellermann et al. |
| 6,231,519 B1 | 5/2001 | Blants et al. |
| 6,267,721 B1 | 7/2001 | Welles |
| 6,283,915 B1 | 9/2001 | Nolan et al. |
| 6,285,816 B1 | 9/2001 | Anderson et al. |
| 6,289,230 B1 | 9/2001 | Chaiken et al. |
| 6,298,314 B1 | 10/2001 | Blackadar et al. |
| 6,332,868 B1 | 12/2001 | Sato et al. |
| 6,358,216 B1 | 3/2002 | Kraus et al. |
| 6,361,660 B1 | 3/2002 | Goldstein |
| 6,371,925 B1 | 4/2002 | Imai et al. |
| 6,374,129 B1 | 4/2002 | Chin et al. |
| 6,415,167 B1 | 7/2002 | Blank et al. |
| 6,443,890 B1 | 9/2002 | Schulze et al. |
| 6,444,474 B1 | 9/2002 | Thomas et al. |
| 6,454,718 B1 | 9/2002 | Clift |
| 6,458,080 B1 | 10/2002 | Brown et al. |
| 6,470,893 B1 | 10/2002 | Boesen |
| 6,513,532 B2 | 2/2003 | Mault et al. |
| 6,514,278 B1 | 2/2003 | Hibst et al. |
| 6,527,711 B1 | 3/2003 | Stivoric et al. |
| 6,527,712 B1 | 3/2003 | Brown et al. |
| 6,529,754 B2 | 3/2003 | Kondo |
| 6,534,012 B1 | 3/2003 | Hazen et al. |
| 6,556,852 B1 * | 4/2003 | Schulze ............ A61B 5/14552 600/310 |
| 6,569,094 B2 | 5/2003 | Suzuki et al. |
| 6,571,117 B1 | 5/2003 | Marbach |
| 6,605,038 B1 | 8/2003 | Teller et al. |
| 6,608,562 B1 | 8/2003 | Kimura et al. |
| 6,616,613 B1 | 9/2003 | Goodman |
| 6,631,196 B1 | 10/2003 | Taenzer et al. |
| 6,635,491 B1 * | 10/2003 | Khalil ................ A61B 5/1455 436/164 |
| 6,647,378 B2 | 11/2003 | Kindo |
| 6,656,116 B2 | 12/2003 | Kim et al. |
| 6,694,180 B1 | 2/2004 | Boesen |
| 6,702,752 B2 | 3/2004 | Dekker |
| 6,725,072 B2 | 4/2004 | Steuer et al. |
| 6,745,061 B1 | 6/2004 | Hicks et al. |
| 6,748,254 B2 | 6/2004 | O'Neil et al. |
| 6,760,610 B2 | 7/2004 | Tschupp et al. |
| 6,783,501 B2 | 8/2004 | Takahashi et al. |
| 6,808,473 B2 | 10/2004 | Hisano et al. |
| 6,859,658 B1 | 2/2005 | Krug |
| 6,893,396 B2 | 5/2005 | Schulze et al. |
| 6,941,239 B2 | 9/2005 | Unuma et al. |
| 6,953,435 B2 | 10/2005 | Kondo et al. |
| 6,954,644 B2 | 10/2005 | Johansson et al. |
| 6,996,427 B2 | 2/2006 | Ali et al. |
| 6,997,879 B1 | 2/2006 | Turcott |
| 7,018,338 B2 | 3/2006 | Vetter et al. |
| 7,024,369 B1 | 4/2006 | Brown et al. |
| 7,030,359 B2 | 4/2006 | Römhild |
| 7,034,694 B2 | 4/2006 | Yamaguchi et al. |
| 7,039,454 B1 | 5/2006 | Kaga et al. |
| 7,041,062 B2 | 5/2006 | Friedrichs et al. |
| 7,043,287 B1 | 5/2006 | Khalil et al. |
| 7,054,674 B2 | 5/2006 | Cane et al. |
| 7,088,234 B2 | 8/2006 | Naito et al. |
| 7,107,088 B2 | 9/2006 | Aceti |
| 7,113,815 B2 | 9/2006 | O'Neil et al. |
| 7,117,032 B2 | 10/2006 | Childre et al. |
| 7,163,512 B1 | 1/2007 | Childre et al. |
| 7,175,601 B2 | 2/2007 | Verjus et al. |
| 7,190,986 B1 | 3/2007 | Hannula et al. |
| 7,209,775 B2 | 4/2007 | Bae et al. |
| 7,217,224 B2 | 5/2007 | Thomas |
| 7,252,639 B2 | 8/2007 | Kimura et al. |
| 7,263,396 B2 | 8/2007 | Chen et al. |
| 7,289,837 B2 | 10/2007 | Mannheimer et al. |
| 7,336,982 B2 | 2/2008 | Yoo et al. |
| 7,341,559 B2 | 3/2008 | Schulz et al. |
| 7,376,451 B2 | 5/2008 | Mahony et al. |
| 7,378,954 B2 | 5/2008 | Wendt |
| 7,470,234 B1 | 12/2008 | Elhag et al. |
| 7,483,730 B2 | 1/2009 | Diab et al. |
| 7,486,988 B2 | 2/2009 | Goodall et al. |
| 7,507,207 B2 | 3/2009 | Sakai et al. |
| 7,519,327 B2 | 4/2009 | White |
| 7,526,327 B2 | 4/2009 | Blondeau et al. |
| 7,583,994 B2 | 9/2009 | Scholz |
| 7,620,450 B2 | 11/2009 | Kim et al. |
| 7,625,285 B2 | 12/2009 | Breving |
| 7,652,569 B2 | 1/2010 | Kiff et al. |
| 7,689,437 B1 | 3/2010 | Teller et al. |
| 7,695,440 B2 | 4/2010 | Kondo et al. |
| 7,725,147 B2 | 5/2010 | Li et al. |
| 7,756,559 B2 | 7/2010 | Abreu |
| 7,843,325 B2 | 11/2010 | Otto |
| 7,894,869 B2 | 2/2011 | Hoarau |
| 7,914,468 B2 | 3/2011 | Shalon et al. |
| 7,991,448 B2 | 8/2011 | Edgar et al. |
| 7,998,079 B2 | 8/2011 | Nagai et al. |
| 8,050,728 B2 | 11/2011 | Al-Ali et al. |
| 8,055,319 B2 | 11/2011 | Oh et al. |
| 8,055,330 B2 | 11/2011 | Egozi |
| 8,059,924 B1 | 11/2011 | Letant et al. |
| 8,130,105 B2 | 3/2012 | Al-Ali et al. |
| 8,137,270 B2 | 3/2012 | Keenan et al. |
| 8,157,730 B2 | 4/2012 | LeBoeuf et al. |
| 8,172,459 B2 | 5/2012 | Abreu |
| 8,175,670 B2 | 5/2012 | Baker, Jr. et al. |
| 8,204,730 B2 | 6/2012 | Liu et al. |
| 8,204,786 B2 | 6/2012 | LeBoeuf et al. |
| 8,233,955 B2 | 7/2012 | Al-Ali et al. |
| 8,251,903 B2 | 8/2012 | LeBoeuf et al. |
| 8,255,027 B2 | 8/2012 | Al-Ali et al. |
| 8,255,029 B2 | 8/2012 | Addison et al. |
| 8,303,512 B2 | 11/2012 | Kosuda et al. |
| 8,320,982 B2 | 11/2012 | LeBoeuf et al. |
| 8,323,982 B2 | 12/2012 | LeBoeuf et al. |
| 8,328,420 B2 | 12/2012 | Abreu |
| 8,416,959 B2 | 4/2013 | Lott et al. |
| 8,491,492 B2 | 7/2013 | Shinar et al. |
| 8,504,679 B2 | 8/2013 | Spire et al. |
| 8,506,524 B2 | 8/2013 | Graskov et al. |
| 8,512,242 B2 | 8/2013 | LeBoeuf et al. |
| 8,647,270 B2 | 2/2014 | LeBoeuf et al. |
| 8,652,040 B2 | 2/2014 | LeBoeuf et al. |
| 8,652,409 B2 | 2/2014 | LeBoeuf et al. |
| 8,679,008 B2 | 3/2014 | Hughes et al. |
| 8,700,111 B2 | 4/2014 | LeBoeuf et al. |
| 8,702,607 B2 | 4/2014 | LeBoeuf et al. |
| 8,730,048 B2 | 5/2014 | Shen et al. |
| 8,788,002 B2 | 7/2014 | LeBoeuf et al. |
| 8,886,269 B2 | 11/2014 | LeBoeuf et al. |

(56) References Cited

U.S. PATENT DOCUMENTS

| | | |
|---|---|---|
| 8,888,701 B2 | 11/2014 | LeBoeuf et al. |
| 8,923,941 B2 | 12/2014 | LeBoeuf et al. |
| 8,929,965 B2 | 1/2015 | LeBoeuf et al. |
| 8,929,966 B2 | 1/2015 | LeBoeuf et al. |
| 8,934,952 B2 | 1/2015 | LeBoeuf et al. |
| 8,942,776 B2 | 1/2015 | LeBoeuf et al. |
| 8,961,415 B2 | 2/2015 | LeBoeuf et al. |
| 9,005,129 B2 | 4/2015 | Venkatraman et al. |
| 2001/0015123 A1 | 8/2001 | Nishitani et al. |
| 2001/0044588 A1 | 11/2001 | Mault |
| 2001/0049471 A1 | 12/2001 | Suzuki et al. |
| 2002/0026108 A1 | 2/2002 | Colvin |
| 2002/0035340 A1 | 3/2002 | Fraden et al. |
| 2002/0143242 A1 | 10/2002 | Nemirovski |
| 2002/0156386 A1 | 10/2002 | Dardik et al. |
| 2002/0156654 A1 | 10/2002 | Roe et al. |
| 2002/0186137 A1 | 12/2002 | Skardon |
| 2002/0188210 A1 | 12/2002 | Aizawa |
| 2002/0194002 A1 | 12/2002 | Petrushin |
| 2003/0002705 A1 | 1/2003 | Boesen |
| 2003/0007631 A1 | 1/2003 | Bolognesi et al. |
| 2003/0045785 A1 | 3/2003 | Diab et al. |
| 2003/0050563 A1 | 3/2003 | Suribhotla et al. |
| 2003/0064712 A1 | 4/2003 | Gaston et al. |
| 2003/0065257 A1 | 4/2003 | Mault et al. |
| 2003/0066269 A1 | 4/2003 | Vetter et al. |
| 2003/0083583 A1 | 5/2003 | Kovtun et al. |
| 2003/0109030 A1 | 6/2003 | Uchida et al. |
| 2003/0109791 A1 | 6/2003 | Kondo et al. |
| 2003/0181795 A1 | 9/2003 | Suzuki et al. |
| 2003/0181798 A1 | 9/2003 | Al-Ali |
| 2003/0212336 A1 | 11/2003 | Lee et al. |
| 2003/0220584 A1 | 11/2003 | Honeyager et al. |
| 2003/0222268 A1 | 12/2003 | Yocom et al. |
| 2003/0233051 A1 | 12/2003 | Verjus et al. |
| 2004/0004547 A1 | 1/2004 | Appelt et al. |
| 2004/0022700 A1 | 2/2004 | Kim et al. |
| 2004/0030581 A1 | 2/2004 | Leven |
| 2004/0034289 A1 | 2/2004 | Teller et al. |
| 2004/0034293 A1 | 2/2004 | Kimball |
| 2004/0039254 A1 | 2/2004 | Stivoric et al. |
| 2004/0054291 A1 | 3/2004 | Schulz et al. |
| 2004/0075677 A1 | 4/2004 | Loyall et al. |
| 2004/0077934 A1 | 4/2004 | Massad |
| 2004/0082842 A1 | 4/2004 | Lumba et al. |
| 2004/0103146 A1 | 5/2004 | Park |
| 2004/0117204 A1 | 6/2004 | Mazar et al. |
| 2004/0120844 A1 | 6/2004 | Tribelsky et al. |
| 2004/0122294 A1 | 6/2004 | Hatlestad et al. |
| 2004/0122702 A1 | 6/2004 | Sabol et al. |
| 2004/0133081 A1 | 7/2004 | Teller |
| 2004/0133123 A1 | 7/2004 | Leonhardt et al. |
| 2004/0135571 A1 | 7/2004 | Uutela et al. |
| 2004/0138578 A1 | 7/2004 | Pineda et al. |
| 2004/0186387 A1 | 9/2004 | Kosuda et al. |
| 2004/0186390 A1 | 9/2004 | Ross et al. |
| 2004/0219056 A1 | 11/2004 | Tribelsky et al. |
| 2004/0220488 A1 | 11/2004 | Vyshedskiy et al. |
| 2004/0225207 A1 | 11/2004 | Bae et al. |
| 2004/0228494 A1 | 11/2004 | Smith |
| 2004/0242976 A1 | 12/2004 | Abreu |
| 2004/0254501 A1 | 12/2004 | Mault |
| 2005/0004458 A1 | 1/2005 | Kanayama et al. |
| 2005/0007582 A1 | 1/2005 | Villers et al. |
| 2005/0021519 A1 | 1/2005 | Ghouri |
| 2005/0027216 A1 | 2/2005 | Guillemaud et al. |
| 2005/0030540 A1 | 2/2005 | Thornton |
| 2005/0033131 A1 | 2/2005 | Chen et al. |
| 2005/0033200 A1 | 2/2005 | Soehren et al. |
| 2005/0036212 A1 | 2/2005 | Saito |
| 2005/0038349 A1 | 2/2005 | Choi et al. |
| 2005/0043600 A1 | 2/2005 | Diab et al. |
| 2005/0043630 A1 | 2/2005 | Honeyager et al. |
| 2005/0058456 A1 | 3/2005 | Yoo |
| 2005/0059870 A1 | 3/2005 | Aceti |
| 2005/0084666 A1 | 4/2005 | Pong et al. |
| 2005/0101845 A1 | 5/2005 | Nihtila |
| 2005/0101872 A1 | 5/2005 | Sattler et al. |
| 2005/0113167 A1 | 5/2005 | Buchner et al. |
| 2005/0113656 A1 | 5/2005 | Chance |
| 2005/0113703 A1 | 5/2005 | Farringdon et al. |
| 2005/0116820 A1 | 6/2005 | Goldreich |
| 2005/0119833 A1 | 6/2005 | Nanikashvili |
| 2005/0148883 A1 | 7/2005 | Boesen |
| 2005/0154264 A1 | 7/2005 | Lecompte et al. |
| 2005/0177034 A1 | 8/2005 | Beaumont |
| 2005/0187448 A1 | 8/2005 | Petersen et al. |
| 2005/0187453 A1 | 8/2005 | Petersen et al. |
| 2005/0192515 A1 | 9/2005 | Givens et al. |
| 2005/0196009 A1 | 9/2005 | Boesen |
| 2005/0203349 A1 | 9/2005 | Nanikashvili |
| 2005/0203357 A1 | 9/2005 | Debreczeny et al. |
| 2005/0209516 A1 | 9/2005 | Fraden |
| 2005/0212405 A1 | 9/2005 | Negley |
| 2005/0222487 A1 | 10/2005 | Miller et al. |
| 2005/0222903 A1 | 10/2005 | Buchheit et al. |
| 2005/0228244 A1 | 10/2005 | Banet |
| 2005/0228299 A1 | 10/2005 | Banet |
| 2005/0228463 A1 | 10/2005 | Mac et al. |
| 2005/0240087 A1 | 10/2005 | Keenan et al. |
| 2005/0245839 A1 | 11/2005 | Stivoric et al. |
| 2005/0258816 A1 | 11/2005 | Zen et al. |
| 2005/0259811 A1 | 11/2005 | Kimm et al. |
| 2006/0009685 A1 | 1/2006 | Finarov et al. |
| 2006/0012567 A1 | 1/2006 | Sicklinger |
| 2006/0063993 A1 | 3/2006 | Yu et al. |
| 2006/0064037 A1 | 3/2006 | Shalon et al. |
| 2006/0084878 A1 | 4/2006 | Banet et al. |
| 2006/0084879 A1 | 4/2006 | Nazarian et al. |
| 2006/0122520 A1 | 6/2006 | Banet et al. |
| 2006/0123885 A1 | 6/2006 | Yates et al. |
| 2006/0140425 A1 | 6/2006 | Berg et al. |
| 2006/0142665 A1 | 6/2006 | Garay et al. |
| 2006/0202816 A1 | 9/2006 | Crump et al. |
| 2006/0205083 A1 | 9/2006 | Zhao |
| 2006/0210058 A1 | 9/2006 | Kock et al. |
| 2006/0211922 A1 | 9/2006 | Al-Ali et al. |
| 2006/0211924 A1 | 9/2006 | Dalke et al. |
| 2006/0217598 A1 | 9/2006 | Miyajima et al. |
| 2006/0224059 A1 | 10/2006 | Swedlow et al. |
| 2006/0240558 A1 | 10/2006 | Zhao |
| 2006/0246342 A1 | 11/2006 | MacPhee |
| 2006/0251277 A1 | 11/2006 | Cho |
| 2006/0251334 A1 | 11/2006 | Oba et al. |
| 2006/0252999 A1 | 11/2006 | Devaul et al. |
| 2006/0264730 A1 | 11/2006 | Stivoric et al. |
| 2006/0292533 A1 | 12/2006 | Selod |
| 2006/0293921 A1 | 12/2006 | McCarthy et al. |
| 2007/0004449 A1 | 1/2007 | Sham |
| 2007/0004969 A1 | 1/2007 | Kong et al. |
| 2007/0015992 A1 | 1/2007 | Filkins et al. |
| 2007/0021206 A1 | 1/2007 | Sunnen |
| 2007/0027367 A1 | 2/2007 | Oliver et al. |
| 2007/0027399 A1 | 2/2007 | Chou |
| 2007/0036383 A1 | 2/2007 | Romero |
| 2007/0050215 A1 | 3/2007 | Kil et al. |
| 2007/0060800 A1 | 3/2007 | Drinan et al. |
| 2007/0060819 A1 | 3/2007 | Altschuler et al. |
| 2007/0063850 A1 | 3/2007 | Devaul et al. |
| 2007/0082789 A1 | 4/2007 | Nissila et al. |
| 2007/0083092 A1 | 4/2007 | Rippo et al. |
| 2007/0083095 A1 | 4/2007 | Rippo et al. |
| 2007/0088221 A1 | 4/2007 | Stahmann |
| 2007/0093702 A1 | 4/2007 | Yu et al. |
| 2007/0106167 A1 | 5/2007 | Kinast |
| 2007/0112273 A1 | 5/2007 | Rogers |
| 2007/0112598 A1 | 5/2007 | Heckerman et al. |
| 2007/0116314 A1 | 5/2007 | Grilliot et al. |
| 2007/0118054 A1 | 5/2007 | Oliver et al. |
| 2007/0123763 A1 | 5/2007 | Al-Ali et al. |
| 2007/0135717 A1 | 6/2007 | Uenishi et al. |
| 2007/0165872 A1 | 7/2007 | Bridger et al. |
| 2007/0167850 A1 | 7/2007 | Russell et al. |
| 2007/0191718 A1 | 8/2007 | Nakamura |

(56) References Cited

U.S. PATENT DOCUMENTS

| | | |
|---|---|---|
| 2007/0197878 A1 | 8/2007 | Shklarski |
| 2007/0197881 A1 | 8/2007 | Wolf et al. |
| 2007/0213020 A1 | 9/2007 | Novac |
| 2007/0230714 A1 | 10/2007 | Armstrong |
| 2007/0233403 A1 | 10/2007 | Alwan et al. |
| 2007/0265097 A1 | 11/2007 | Havukainen |
| 2007/0270667 A1 | 11/2007 | Coppi et al. |
| 2007/0270671 A1 | 11/2007 | Gal |
| 2007/0293781 A1 | 12/2007 | Sims et al. |
| 2007/0299330 A1 | 12/2007 | Couronne et al. |
| 2008/0001735 A1 | 1/2008 | Tran |
| 2008/0004536 A1 | 1/2008 | Baxi et al. |
| 2008/0015424 A1 | 1/2008 | Bernreuter |
| 2008/0039731 A1 | 2/2008 | McCombie et al. |
| 2008/0076972 A1 | 3/2008 | Dorogusker et al. |
| 2008/0081963 A1 | 4/2008 | Naghavi et al. |
| 2008/0081972 A1 | 4/2008 | Debreczeny |
| 2008/0086533 A1 | 4/2008 | Neuhauser et al. |
| 2008/0096726 A1 | 4/2008 | Riley et al. |
| 2008/0114220 A1 | 5/2008 | Banet et al. |
| 2008/0132798 A1 | 6/2008 | Hong et al. |
| 2008/0133699 A1 | 6/2008 | Craw et al. |
| 2008/0141301 A1 | 6/2008 | Azzaro et al. |
| 2008/0146890 A1 | 6/2008 | LeBoeuf et al. |
| 2008/0154098 A1 | 6/2008 | Morris et al. |
| 2008/0154105 A1 | 6/2008 | Lemay |
| 2008/0165017 A1* | 7/2008 | Schwartz ............ A61B 5/6815 340/573.1 |
| 2008/0170600 A1 | 7/2008 | Sattler et al. |
| 2008/0171945 A1 | 7/2008 | Dotter |
| 2008/0177162 A1 | 7/2008 | Bae et al. |
| 2008/0200774 A1 | 8/2008 | Luo |
| 2008/0203144 A1 | 8/2008 | Kim |
| 2008/0221461 A1 | 9/2008 | Zhou et al. |
| 2008/0249594 A1 | 10/2008 | Dietrich |
| 2008/0287752 A1 | 11/2008 | Stroetz et al. |
| 2009/0005662 A1 | 1/2009 | Petersen et al. |
| 2009/0006457 A1 | 1/2009 | Stivoric et al. |
| 2009/0010461 A1 | 1/2009 | Klinghult et al. |
| 2009/0010556 A1 | 1/2009 | Uchibayashi et al. |
| 2009/0030350 A1 | 1/2009 | Yang et al. |
| 2009/0054751 A1 | 2/2009 | Babashan et al. |
| 2009/0054752 A1 | 2/2009 | Jonnalagadda et al. |
| 2009/0069645 A1 | 3/2009 | Nielsen et al. |
| 2009/0082994 A1 | 3/2009 | Schuler et al. |
| 2009/0088611 A1 | 4/2009 | Buschmann |
| 2009/0093687 A1 | 4/2009 | Telfort et al. |
| 2009/0105548 A1 | 4/2009 | Bart |
| 2009/0105556 A1 | 4/2009 | Fricke et al. |
| 2009/0131761 A1 | 5/2009 | Moroney, III et al. |
| 2009/0131764 A1 | 5/2009 | Lee et al. |
| 2009/0163787 A1* | 6/2009 | Mannheimer ...... A61B 5/14552 600/324 |
| 2009/0175456 A1 | 7/2009 | Johnson |
| 2009/0177097 A1 | 7/2009 | Ma et al. |
| 2009/0214060 A1 | 8/2009 | Chuang et al. |
| 2009/0221888 A1 | 9/2009 | Wijesiriwardana |
| 2009/0227853 A1 | 9/2009 | Wijesiriwardana |
| 2009/0240125 A1 | 9/2009 | Such et al. |
| 2009/0253992 A1 | 10/2009 | Van Der Loo |
| 2009/0253996 A1 | 10/2009 | Lee et al. |
| 2009/0264711 A1 | 10/2009 | Schuler et al. |
| 2009/0270698 A1 | 10/2009 | Shioi et al. |
| 2009/0275813 A1 | 11/2009 | Davis |
| 2009/0281435 A1 | 11/2009 | Ahmed et al. |
| 2009/0287067 A1 | 11/2009 | Dorogusker et al. |
| 2009/0299215 A1 | 12/2009 | Zhang |
| 2010/0004517 A1 | 1/2010 | Bryenton et al. |
| 2010/0022861 A1 | 1/2010 | Cinbis et al. |
| 2010/0045663 A1 | 2/2010 | Chen et al. |
| 2010/0100013 A1 | 4/2010 | Hu et al. |
| 2010/0113948 A1 | 5/2010 | Yang et al. |
| 2010/0168531 A1 | 7/2010 | Shaltis et al. |
| 2010/0172522 A1 | 7/2010 | Mooring et al. |
| 2010/0179389 A1 | 7/2010 | Moroney et al. |
| 2010/0185105 A1 | 7/2010 | Baldinger |
| 2010/0217100 A1 | 8/2010 | LeBoeuf |
| 2010/0217103 A1 | 8/2010 | Abdul-Hafiz et al. |
| 2010/0222655 A1 | 9/2010 | Starr et al. |
| 2010/0228315 A1 | 9/2010 | Nielsen |
| 2010/0234714 A1 | 9/2010 | Mercier et al. |
| 2010/0268056 A1 | 10/2010 | Picard et al. |
| 2010/0274100 A1 | 10/2010 | Behar et al. |
| 2010/0274109 A1 | 10/2010 | Hu et al. |
| 2010/0292589 A1 | 11/2010 | Goodman |
| 2010/0298653 A1 | 11/2010 | McCombie et al. |
| 2011/0028810 A1 | 2/2011 | Van Slyke et al. |
| 2011/0028813 A1 | 2/2011 | Watson et al. |
| 2011/0081037 A1 | 4/2011 | Oh et al. |
| 2011/0098112 A1 | 4/2011 | LeBoeuf |
| 2011/0105869 A1 | 5/2011 | Wilson et al. |
| 2011/0112382 A1 | 5/2011 | Li et al. |
| 2011/0130638 A1 | 6/2011 | Raridan, Jr. |
| 2011/0142371 A1 | 6/2011 | King et al. |
| 2011/0288379 A1 | 11/2011 | Wu |
| 2012/0030547 A1 | 2/2012 | Raptis et al. |
| 2012/0095303 A1 | 4/2012 | He |
| 2012/0116231 A1 | 5/2012 | Liao et al. |
| 2012/0150052 A1 | 6/2012 | Buchheim et al. |
| 2012/0156933 A1 | 6/2012 | Kreger et al. |
| 2012/0179011 A1 | 7/2012 | Moon et al. |
| 2012/0197093 A1 | 8/2012 | LeBoeuf et al. |
| 2012/0203081 A1 | 8/2012 | LeBoeuf et al. |
| 2012/0226111 A1 | 9/2012 | LeBoeuf et al. |
| 2012/0226112 A1 | 9/2012 | LeBoeuf et al. |
| 2012/0277548 A1 | 11/2012 | Burton |
| 2012/0283577 A1 | 11/2012 | LeBoeuf et al. |
| 2012/0296184 A1 | 11/2012 | LeBoeuf et al. |
| 2013/0053661 A1 | 2/2013 | Alberth et al. |
| 2013/0072765 A1 | 3/2013 | Kahn et al. |
| 2013/0245387 A1 | 9/2013 | Patel |
| 2013/0336495 A1 | 12/2013 | Burgett et al. |
| 2014/0012105 A1 | 1/2014 | LeBoeuf et al. |
| 2014/0051940 A1 | 2/2014 | Messerschmidt |
| 2014/0051948 A1 | 2/2014 | LeBoeuf et al. |
| 2014/0052567 A1 | 2/2014 | Bhardwaj et al. |
| 2014/0058220 A1 | 2/2014 | LeBoeuf et al. |
| 2014/0073486 A1 | 3/2014 | Ahmed et al. |
| 2014/0094663 A1 | 4/2014 | LeBoeuf et al. |
| 2014/0100432 A1 | 4/2014 | Golda et al. |
| 2014/0114147 A1 | 4/2014 | Romesburg et al. |
| 2014/0127996 A1 | 5/2014 | Park et al. |
| 2014/0128690 A1 | 5/2014 | LeBoeuf et al. |
| 2014/0135596 A1 | 5/2014 | LeBoeuf et al. |
| 2014/0140567 A1 | 5/2014 | LeBoeuf et al. |
| 2014/0219467 A1 | 8/2014 | Kurtz |
| 2014/0235967 A1 | 8/2014 | LeBoeuf et al. |
| 2014/0235968 A1 | 8/2014 | LeBoeuf et al. |
| 2014/0236531 A1 | 8/2014 | Carter |
| 2014/0243617 A1 | 8/2014 | LeBoeuf et al. |
| 2014/0243620 A1 | 8/2014 | LeBoeuf et al. |
| 2014/0275852 A1 | 9/2014 | Hong et al. |
| 2014/0275855 A1 | 9/2014 | LeBoeuf et al. |
| 2014/0287833 A1 | 9/2014 | LeBoeuf et al. |
| 2014/0288396 A1 | 9/2014 | LeBoeuf et al. |
| 2014/0288436 A1 | 9/2014 | Venkatraman et al. |
| 2014/0323829 A1 | 10/2014 | LeBoeuf et al. |
| 2014/0323830 A1 | 10/2014 | LeBoeuf et al. |
| 2014/0323880 A1 | 10/2014 | Ahmed et al. |
| 2014/0378844 A1 | 12/2014 | Fei |
| 2015/0031967 A1 | 1/2015 | LeBoeuf et al. |
| 2015/0032009 A1 | 1/2015 | LeBoeuf et al. |
| 2015/0250396 A1 | 9/2015 | Ahmed et al. |
| 2015/0265217 A1 | 9/2015 | Penders et al. |
| 2015/0289820 A1 | 10/2015 | Miller et al. |
| 2015/0342481 A1 | 12/2015 | Liu et al. |
| 2016/0022220 A1 | 1/2016 | Lee et al. |
| 2016/0029964 A1 | 2/2016 | LeBoeuf et al. |
| 2016/0094899 A1 | 3/2016 | Aumer et al. |

(56) References Cited

U.S. PATENT DOCUMENTS

| | | | |
|---|---|---|---|
| 2016/0287108 | A1 | 10/2016 | Wei et al. |
| 2017/0034615 | A1 | 2/2017 | Mankodi et al. |

FOREIGN PATENT DOCUMENTS

| | | |
|---|---|---|
| CN | 201438747 U | 4/2010 |
| DE | 3910749 A1 | 10/1990 |
| EP | 1 297 784 A1 | 4/2003 |
| EP | 1 480 278 A2 | 11/2004 |
| EP | 2 077 091 A2 | 7/2009 |
| EP | 2 182 839 B1 | 10/2011 |
| GB | 2 408 209 A | 5/2005 |
| GB | 2 411 719 A | 9/2005 |
| JP | 7-241279 | 9/1995 |
| JP | 9-253062 | 9/1997 |
| JP | 9-299342 | 11/1997 |
| JP | 2000-116611 | 4/2000 |
| JP | 2001-025462 | 1/2001 |
| JP | 20030159221 | 6/2003 |
| JP | 2004-513750 A | 5/2004 |
| JP | 2004-283523 | 10/2004 |
| JP | 2005-040261 A | 2/2005 |
| JP | 2005-270544 A | 10/2005 |
| JP | 2007-044203 | 2/2007 |
| JP | 2007-185348 | 7/2007 |
| JP | 2008-136556 A | 6/2008 |
| JP | 2008-279061 A | 11/2008 |
| JP | 2009-153664 A | 7/2009 |
| JP | 2010-526646 | 8/2010 |
| JP | 2014-068733 A | 4/2014 |
| KR | 20-0204510 Y1 | 11/2000 |
| WO | WO 00/24064 | 4/2000 |
| WO | WO 2000/047108 A1 | 8/2000 |
| WO | WO 01/08552 A1 | 2/2001 |
| WO | WO 2002/017782 A2 | 3/2002 |
| WO | WO 2005/010568 A2 | 2/2005 |
| WO | WO 2005/020121 A1 | 3/2005 |
| WO | WO 2005/03212 A2 | 4/2005 |
| WO | WO 2005/110238 A1 | 11/2005 |
| WO | WO 2006/009830 A2 | 1/2006 |
| WO | WO 2006/067690 A2 | 6/2006 |
| WO | WO 2007/012931 A2 | 2/2007 |
| WO | WO 2007/038432 A2 | 4/2007 |
| WO | WO 2007/053146 A1 | 5/2007 |
| WO | WO 2008/141306 A2 | 11/2008 |
| WO | WO 2011/094875 A1 | 8/2011 |
| WO | WO 2011/127063 A1 | 10/2011 |
| WO | WO 2013/038296 A1 | 3/2013 |
| WO | WO 2014/092932 A1 | 6/2014 |

OTHER PUBLICATIONS

Extended European Search Report, EP Application No. 16164775.5 dated Sep. 13, 2016, 7 pages.
Notification of Transmittal of the International Search Report and the Written Opinion of the International Searching Authority, or the Declaration, PCT/US2016/041842, dated Oct. 21, 2016, 5 pages.
Notification of Transmittal of International Preliminary Report on Patentability, PCT/US2015/041562, dated Oct. 20, 2016, 14 pages.
Notification of Transmittal of International Preliminary Report on Patentability, PCT/US2015/042636, dated Oct. 20, 2016, 7 pages.
Notification of Transmittal of International Preliminary Report on Patentability, PCT/US2015/042015, dated Oct. 20, 2016, 10 pages.
Notification of Transmittal of International Preliminary Report on Patentability, PCT/US2015/042035, dated Oct. 20, 2016, 8 pages.
Notification of Transmittal of International Preliminary Report on Patentability, PCT/US2015/046079, dated Oct. 20, 2016, 10 pages.
Webster, J. G. Design of Pulse Oximeters. IOP Publishing Ltd., 1997, Cover page, pp. i-xvi, pp. 34-159.
Communication with Supplementary European Search Report, European Application No. 15830336.2, dated Jun. 7, 2017, 8 pp.
Asada et al., "Mobile Monitoring with Wearable Photoplethysmographic Biosensors", *IEEE Engineering in Medicine and Biology Magazine*, May/Jun. 2003, pp. 28-40.
Han et al., "Development of a wearable health monitoring device with motion artifact reduced algorithm" *International Conference on Control, Automation and Systems 2007 (ICCAS 2007)*, Seoul, Korea, Oct. 17-20, 2007, pp. 1581-1584.
Comtois et al., "A Comparative Evaluation of Adaptive Noise Cancellation Algorithms for Minimizing Motion Artifacts in a Forehead-Mounted Wearable Pluse Oximeter", *Proceedings of the 29th Annual International Conference of the IEEE EMBS*, Lyon, France, Aug. 23-26, 2007, pp. 1528-1531.
Lee et al., "A Mobile Care System With Alert Mechanism", *IEEE Transactions on Information Technology in Biomedicine*, vol. 11, No. 5, Sep. 2007, pp. 507-517.
Notification of Transmittal of the International Search Report and the Written Opinion of the International Searching Authority, or the Declaration, PCT/US2015/046079, dated Dec. 29, 2015.
Communication pursuant to Article 94(3) EPC, European Patent Application No. 13863449.8, dated Nov. 5, 2015, 7 pages.
Communication pursuant to Article 94(3) EPO, European Patent Application No. 14743615.8, dated Dec. 23, 2015, 7 pages.
Communication pursuant to Article 94(3) EPC, European Patent Application No. 14743839.4, dated Dec. 23, 2015, 6 pages.
Asada, et al., "Mobile Monitoring with Wearable Photoplethysmographic Biosensors," IEEE Engineering in Medicine and Biology Magazine, May/Jun. 2003, pp. 28-40.
Bifulco et al., "Bluetooth Portable Device for Continuous ECG and Patient Motion Monitoring During Daily Life," Medicon 2007, IFMBE Proceedings 16, 2007, pp. 369-372.
Brodersen et al., "In-Ear Acquisition of Vital Signs Discloses New Chances for Preventive Continuous Cardiovascular Monitoring," 4th International Workshop on Wearable and Implantable Body Sensor Networks (BSN 2007), vol. 13 of the series IFMBE Proceedings, pp. 189-194.
Celka et al, "Motion Resistant Earphone Located Infrared based Heart Rate Measurement Device," Proceedings of the Second IASTED International Conference on Biomedical Engineering, Feb. 16-18, 2004, Innsbruck, Austria, pp. 582-585.
Communication Pursuant to Article 94(3) EPC, EP 12 739 502.8, dated Jul. 19, 2016, 7 pages.
Communication Pursuant to Article 94(3) EPC, EP 14 743 615.8, dated Jul. 19, 2016, 7 pages.
Communication Pursuant to Article 94(3) EPC, EP 14 743 839.4, dated Jul. 20, 2016, 5 pages.
Comtois et al., "A Wearable Wireless Reflectance Pulse Oximeter for Remote Triage Applications," 2006 IEEE, pp. 53-54.
Comtois, Gary, W., "Implementation of Accelerometer-Based Adaptive Noise Cancellation in a Wireless Wearable Pulse Oximeter Platform for Remote Physiological Monitoring and Triage," Thesis, Worcester Polytechnic Institute, Aug. 31, 2007, 149 pages.
Duun et al., "A Novel Ring Shaped Photodiode for Reflectance Pulse Oximetry in Wireless Applications," IEEE Sensors 2007 Conference, pp. 596-599.
Geun et al., "Measurement Site and Applied Pressure Consideration in Wrist Photoplethysmography," The 23rd International Technical Conference on Circuits/Systems, Computers and Communications, 2008, pp. 1129-1132.
Gibbs et al., "Active motion artifact cancellation for wearable health monitoring sensors using collocated MEMS accelerometers," Smart Structures and Materials, 2005: Sensors and Smart Structures Technologies for Civil, Mechanical, and Aerospace Systems, Proc. of SPIE, vol. 5765, pp. 811-819.
Haahr et al., "A Wearable "Electronic Patch" for Wireless Continuous Monitoring of Chronically Diseased Patients," Proceedings of the 5th International Workshop on Wearable and Implantable Body Sensor Networks, in conjunction with The 5th International Summer School and Symposium on Medical Devices and Biosensors, The Chinese University of Hong Kong, HKSAR, China, Jun. 1-3, 2008, pp. 66-70.
Jiang, Honghui, "Motion-Artifact Resistant Design of Photoplethysmograph Ring Sensor for Driver Monitoring," Thesis, Massachusetts Institute of Technology, Feb. 2004, 62 pages.

(56) References Cited

OTHER PUBLICATIONS

Kuzmina et al., "Compact multi-functional skin spectrometry set-up," Advanced Optical Materials, Technologies, and Devices, Proc. of SPIE, vol. 6596, 2007, pp. 65960T-1 to 65960T-6.

Lee et al, "Respiratory Rate Detection Algorithms by Photoplethysmography Signal Processing," 30th Annual International IEEE EMBS Conference, Vancouver, British Columbia, Canada, Aug. 20-24, 2008, pp. 1140-1143.

Lindberg et al., "Monitoring of respiratory and heart rates using a fibre-optic sensor," Med Biol Eng Comput, Sep. 1992, vol. 30, No. 5, pp. 533-537.

Luprano, Jean, "Sensors and Parameter Extraction by Wearable Systems: Present Situation and Future," pHealth 2008, May 21, 2008, 29 pages.

Lygouras et al., "Optical-Fiber Finger Photo-Plethysmograph Using Digital Techniques," IEEE Sensors Journal, vol. 2, No. 1, Feb. 2002, pp. 20-25.

Maguire et al., "The Design and Clinical Use of a Reflective Brachial Photoplethysmograph," Technical Report NUIM/SS/-/2002/04, Submitted Apr. 2002, Signals and Systems Research Group, National University of Ireland, Maynooth, Co. Kildare, Ireland, 13 pages.

Mendelson et al., "Measurement Site and Photodetector Size Considerations in Optimizing Power Consumption of a Wearable Reflectance Pulse Oximeter," Proceedings of the 25th Annual International Conference of the IEEE EMBS, Cancun, Mexico, Sep. 17-21, 2003, pp. 3016-3019.

Mendelson et al., "Noninvasive Pulse Oximetry Utilizing Skin Reflectance Photoplethysmography," IEEE Transactions on Biomedical Engineering, vol. 35, No. 10, Oct. 1988, pp. 798-805.

Poh et al., "Motion Tolerant Magnetic Earring Sensor and Wireless Earpiece for Wearable Photoplethysmography," IEEE Transactions on Information Technology in Biomedicine, vol. 14, No. 3, May 2010, pp. 786-794.

Renevey et al., "Wrist-Located Pulse Detection Using IR Signals, Activity and Nonlinear Artifact Cancellation," IEEE EMBS, 2001, 4 pages.

Rhee et al., "Artifact-Resistant Power-Efficient Design of Finger-Ring Plethysmographic Sensors," IEEE Transactions on Biomedical Engineering, vol. 48, No. 7, Jul. 2001, pp. 795-805.

Shaltis, Phillip Andrew, Analysis and Validation of an Artifact Resistant Design for Oxygen Saturation Measurement Using Photo Plethysmographic Ring Sensors, Thesis, Massachusetts Institute of Technology, Jun. 2004, 103 pages.

Shin et al., "A Novel Headset with a Transmissive PPG Sensor for Heart Rate Measurement," ICBME 2008, Proceedings 23, 2009, pp. 519-522.

Spigulis et al, "Wearable wireless photoplethysmography sensors," Proc. of SPIE, vol. 6991, 2008, pp. 69912O-1 to 69912O-7.

Takatani et al., "Optical Oximetry Sensors for Whole Blood and Tissue," IEEE Engineering in Medicine and Biology, Jun./Jul. 1994, pp. 347-357.

Vogel et al., "A System for Assessing Motion Artifacts in the Signal of a Micro-Optic In-Ear Vital Signs Sensor," 30th Annual International IEEE EMBS Conference, Vancouver, British Columbia, Canada, Aug. 20-24, 2008.

Vogel et al., "In-Ear Heart Rate Monitoring Using a Micro-Optic Reflective Sensor," Proceedings of the 29th Annual International Conference of the IEEE EMBS Cite Internationale, Lyon, France, Aug. 23-26, 2007, pp. 1375-1378.

Wang et al., "Multichannel Reflective PPG Earpiece Sensor With Passive Motion Cancellation," IEEE Transactions on Biomedical Circuits and Systems, vol. 1, No. 4, Dec. 2007, pp. 235-241.

Wang et al., "Reflective Photoplethysmograph Earpiece Sensor for Ubiquitous Heart Rate Monitoring," 4th International Workshop on Wearable and Implantable Body Sensor Networks, 2007, vol. 13 of the series IFMBE Proceedings, pp. 179-183.

Wei et al. "A New Wristband Wearable Sensor Using Adaptive Reduction Filter to Reduce Motion Artifact," Proceedings of the 5th International Conference on Information Technology and Application in Biomedicine, in conjunction with The 2nd International Symposium & Summer School on Biomedical and Health Engineering, Shenzhen, China, May 30-31, 2008, pp. 278-281.

Wood, Levi Benjamin, "Motion Artifact Reduction for Wearable Photoplethysmogram Sensors Using Micro Accelerometers and Laguerre Series Adaptive Filters," Thesis, Massachusetts Institute of Technology, Jun. 2008, 74 pages.

Communication pursuant to Article 94(3) EPC, European Patent Application No. 12820308.0, dated Feb. 3, 2016, 5 pages.

Notification of Transmittal of the International Search Report and Written Opinion of the International Search Authority dated May 26, 2016 by the Korean Intellectual Property Office for corresponding International Application No. PCT/US2016/019126.

Notification of Transmittal of the International Search Report and Written Opinion of the International Search Authority dated May 26, 2016 by the Korean Intellectual Property Office for corresponding International Application No. PCT/US2016/019132.

Edmison et al., "E-Textile Based Automatic Activity Diary for Medical Annotation and Analysis," Proc. BSN 2006 Int. Workshop Wearable Implantable Body Sensor Netw. (2006), pp. 131-145, Apr. 3-5, 2006.

European Search Report, EP Application No. 13863449.8, dated Oct. 19, 2015, 3 pages.

European Search Report, EP Application No. 14743615.8, dated Oct. 12, 2015, 3 pages.

European Search Report, EP Application No. 14743839.4, dated Oct. 12, 2015, 3 pages.

Gibbs et al., "Reducing Motion Artifact in Wearable Bio-Sensors Using MEMS Accelerometers for Active Noise Cancellation," 2005 American Control Conference, Jun. 8-10, 2005, Portland, OR, USA, pp. 1581-1586.

International Preliminary Report on Patentability, PCT/US2014/012940, dated Jun. 17, 2015, 23 pages.

International Search Report and Written Opinion of the International Searching Authority, corresponding to International Patent Application No. PCT/US2014/012940, dated Oct. 16, 2014, 13 pages.

International Search Report corresponding to International Patent Application No. PCT/US2014/012909, dated May 13, 2014, 3 pages.

Notification Concerning Transmittal of International Preliminary Report on Patentability, PCT/US2014/012909, dated Jul. 28, 2015.

Notification of Transmittal of the International Search Report and the Written Opinion of the International Searching Authority, or the Declaration, PCT/US2015/014562, dated Oct. 28, 2015.

Notification of Transmittal of the International Search Report and the Written Opinion of the International Searching Authority, or the Declaration, PCT/US2015/042636, dated Oct. 29, 2015.

Notification of Transmittal of the International Search Report and the Written Opinion of the International Searching Authority, or the Declaration, PCT/US2015/042015, dated Oct. 29, 2015.

Notification of Transmittal of the International Search Report and the Written Opinion of the International Searching Authority, or the Declaration, PCT/US2015/042035, dated Oct. 29, 2015.

Wood et al., "Active Motion Artifact Reduction for Wearable Sensors Using Laguerre Expansion and Signal Separation," Proceedings of the 2005 IEEE Engineering in Medicine and Biology, 27th Annual Conference, Shanghai, China, Sep. 1-4, 2005, pp. 3571-3574.

"U.S. Army Fitness Training Handbook" by the Department of the Army, 2003, The Lyons Press. p. 17.

"Warfighter Physiological and Environmental Monitoring: A Study for the U.S. Army Research Institute in Environmental Medicine and the Soldier Systems Center", Massachusetts Institute of Technology Lincoln Laboratory, Final Report, Nov. 1, 2004, prepared for the U.S. Army under Air Force Contract F19628-00-C-0002; approved for public release.

Anpo et al. "Photocatalytic Reduction of $Co_2$ With $H_2O$ on Titanium Oxides Anchored within Micropores of Zeolites: Effects of the Structure of the Active Sites and the Addition of Pt" *J. Phys. Chem. B*, 101:2632-2636 (1997).

(56) References Cited

OTHER PUBLICATIONS

Bârsan et al. "Understanding the fundamental principles of metal oxide based gas sensors; the example of CO sensing with $SnO_2$ sensors in the presence of humidity" *Journal of Physics: Condensed Matter* 15:R813-R839 (2003).
Bott "Electrochemistry of Semiconductors" *Current Separations* 17(3):87-91 (1998).
Colligan, M. J. et al. in "The psychological effects of indoor air pollution", Bulletin of the New York Academy of Medicine, vol. 57, No. 10, Dec. 1981, p. 1014-1026.
de Paula Santos, U. et al, in "Effects of air pollution on blood pressure and heart rate variability: a panel study of vehicular traffic controllers in the city of Sao Paulo, Brazil", European Heart Journal (2005) 26, 193-200.
Ebert, T et al., "Influence of Hydration Status on Thermoregulation and Cycling Hill Climbing," Med. Sci. Sport Exerc. vol. 39, No. 2, pp. 323-329, 2007.
European Search Report corresponding to European Application No. 07862660.3 dated Apr. 25, 2012; 7 pages.
Falkner et al, "Cardiovascular response to mental stress in normal adolescents with hypertensive parents. Hemodynamics and mental stress in adolescents," *Hypertension* 1979, 1:23-30.
FiTrainer "The Only Trainer You Need"; http://itami.com; Downloaded Feb. 26, 2010; © 2008 FiTriainer™; 2 pages.
Fleming et al., "A Comparison of Signal Processing Techniques for the Extraction of Breathing Rate from the Photopethysmorgram," World Academy of Science, Engineering and Technology, vol. 30, Oct. 2007, pp. 276-280.
Geladas et al., "Effect of cold air inhalation on core temperature in exercising subjects under stress," The American Physiological Society, pp. 2381-2387, 1988.
Gold, D.R. et al. in "Ambient Pollution and Heart Rate Variability", Circulation 2000, 101:1267-1273.
International Search Report corresponding to International Patent Application No. PCT/US2012/046446, dated Jan. 14, 2013, 3 pages.
International Search Report and Written Opinion of the International Searching Authority, corresponding to PCT/US2012/0948079, dated Oct. 9, 2012.
International Search Report and Written Opinion of the International Searching Authority, corresponding to PCT/US2007/025114, dated May 13, 2008.
International Search Report Corresponding to International Application No. PCT/US2012/022634, dated Aug. 22, 2012, 9 pages.
Maomao et al., "Mobile Context-Aware Game for the Next Generation," $2^{nd}$ International Conference on Application and Development of Computer Games ADCOG 2003, p. 78-81.
Martins et al. "Zinc oxide as an ozone sensor" *Journal of Applied Physics* 96(3):1398-1408.
Maughan, R.J., "Impact of mild dehydration on wellness and on exercise performance," European Journal of Clinical Nutrition, 57, Suppl. 2, pp. S19-S23, 2003.
Maughan et al., "Exercise, Heat, Hydration and the Brain," Journal of the American College of Nutrition, vol. 26, No. 5, pp. 604S-612S, 2007.
Mostardi, R., et al., "The effect of increased body temperature due to exercise on the heart rate and the maximal aerobic power," Europ. J. Appl. Physiol, 33, pp. 237-245, 1974.
Nakajima et al., "Monitoring of heart and respiratory rates by photoplethyusmography using a digital filtering technique," Med. Eng. Phys., vol. 18, No. 5, Jul. 1996, pp. 365-372.
Notification of Transmittal of the International Search Report and Written Opinion of the International Search Authority dated Jul. 30, 2010 by the Korean Intellectual Property Office for corresponding International Application No. PCT/US2010/021936.
Notification of Transmittal of the International Search Report and Written Opinion of the International Search Authority dated Aug. 26, 2010 by the Korean Intellectual Property Office for corresponding International Application No. PCT/US2010/021629.
Notification of Transmittal of the International Search Report and the Written Opinion of the International Search Authority dated Sep. 16, 2010 by the Korean Intellectual Property Office for corresponding International Application No. PCT/US2010/024922.
Notification of Transmittal of the International Search Report and the Written Opinion of the International Search Authority dated Sep. 27, 2010 by the Korean Intellectual Property Office for corresponding International Application No. PCT/US2010/025216.
Notification of Transmittal of the International Search Report and The Written Opinion of the International Searching Authority, or the Declaration corresponding to International Application No. PCT/US2013/070271; dated Feb. 26, 2014; 13 pages.
Saladin et al. "Photosynthesis of $CH_4$ at a $TiO_2$ Surface from Gaseous $H_2O$ and $CO_2$" *J. Chem. Soc., Chem. Commun.* 533-534 (1995).
Shorten et al., "Acute effect of environmental temperature during exercise on subsequent energy intake in active men," Am. J Clin. Nutr. 90, pp. 1215-21, 2009.
Skubal et al. "Detection and identification of gaseous organics using a $TiO_2$ sensor" *Journal of Photochemistry and Photobiology A: Chemistry* 148:103-108 (2002).
Skubal et al. "Monitoring the Electrical Response of Photoinduced Organic Oxideation on TiO2 Surfaces" Manuscript submitted Oct. 2000 to SPIE Intl. Symposium on Environment & Industrial Sensing, Boston, MA, Nov. 5-8, 2000, sponsored by SPIE, 10 pp.
Thompson, M.W., "Cardiovascular drift and critical core temperature: factors limiting endurance performance in the heat?" J. Exerc. Sci. Fit, vol. 4, No. 1, pp. 15-24, 2006.
Zhang et al. "Development of Chemical Oxygen Demand On-Line Monitoring System Based on a Photoelectrochemical-Degradation Principle" *Environ. Sci. Technol.*, 40(7):2363-2368 (2006).

\* cited by examiner

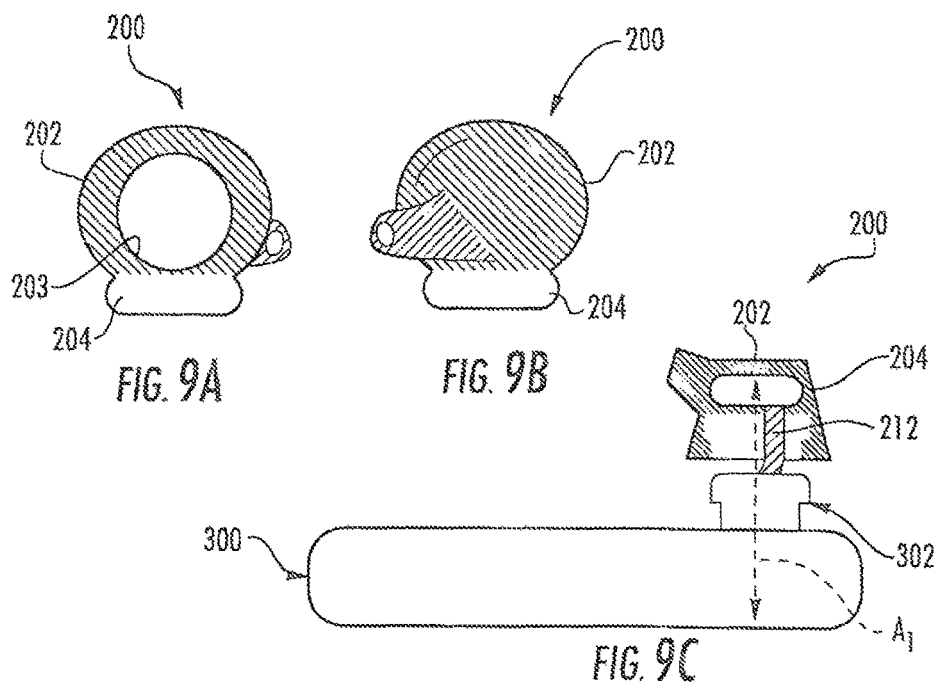
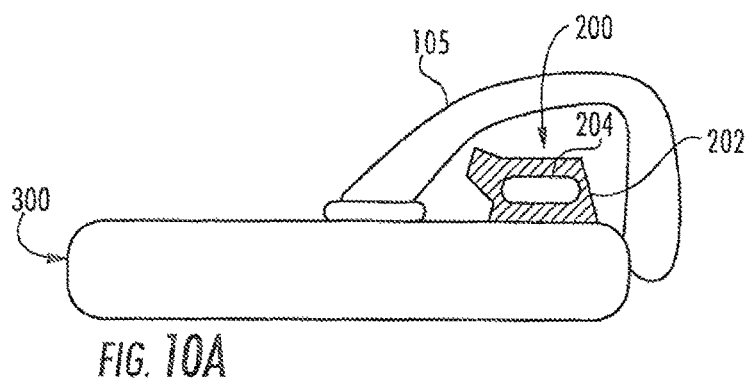
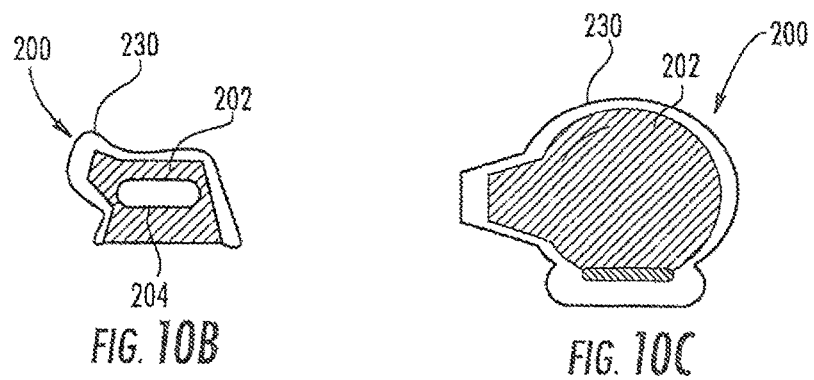

METHODS AND APPARATUS FOR DETECTING MOTION NOISE AND FOR REMOVING MOTION NOISE FROM PHYSIOLOGICAL SIGNALS

RELATED APPLICATIONS

This application is a continuation application of pending U.S. patent application Ser. No. 14/159,156, filed Jan. 20, 2014, which is a divisional application of U.S. patent application Ser. No. 12/692,807, filed Jan. 25, 2010, now U.S. Pat. No. 8,647,270, which claims the benefit of and priority to U.S. Provisional Patent Application No. 61/208,567 filed Feb. 25, 2009, U.S. Provisional Patent Application No. 61/208,574 filed Feb. 25, 2009, U.S. Provisional Patent Application No. 61/212,444 filed Apr. 13, 2009, and U.S. Provisional Patent Application No. 61/274,191 filed Aug. 14, 2009, the disclosures of which are incorporated herein by reference as if set forth in their entireties.

FIELD OF THE INVENTION

The present invention relates generally to health and environmental monitoring and, more particularly, to health and environmental monitoring apparatus.

BACKGROUND OF THE INVENTION

There is growing market demand for personal health and environmental monitors, for example, for gauging overall health and metabolism during exercise, athletic training, dieting, daily life activities, sickness, and physical therapy. However, traditional health monitors and environmental monitors may be bulky, rigid, and uncomfortable—generally not suitable for use during daily physical activity. There is also growing interest in generating and comparing health and environmental exposure statistics of the general public and particular demographic groups. For example, collective statistics may enable the healthcare industry and medical community to direct healthcare resources to where they are most highly valued. However, methods of collecting these statistics may be expensive and laborious, often utilizing human-based recording/analysis steps at multiple sites.

As such, improved ways of collecting, storing and analyzing physiological information are needed. In addition, improved ways of seamlessly extracting physiological information from a person during everyday life activities, especially during high activity levels, may be important for enhancing fitness training and healthcare quality, promoting and facilitating prevention, and reducing healthcare costs.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, a monitoring apparatus includes a housing that is configured to be attached to a body of a subject, and that has a sensor region that is configured to contact a selected area of the body of the subject when the housing is attached to the body of the subject. The sensor region is contoured (i.e., is "form-fitted") to matingly engage the selected body area. The apparatus includes at least one physiological sensor that is associated with the sensor region and that detects and/or measures physiological information from the subject and/or at least one environmental sensor associated with the sensor region that is configured to detect and/or measure environmental information. The sensor region contour stabilizes the physiological and/or environmental sensor(s) relative to the selected body area such that subject motion does not negatively impact detection and/or measurement efforts of the sensor(s). In some embodiments, the sensor region contour stabilizes the housing of the monitoring apparatus when the housing is attached to the body of the subject. An exemplary monitoring apparatus, according to embodiments of the present invention is a headset having an earbud module and wherein the sensor region is a portion of the housing of the earbud module.

The sensor region of a monitoring apparatus, according to some embodiments of the present invention, can have various characteristics. For example, in some embodiments, at least a portion of the sensor region is detachable from the housing. In some embodiments, at least a portion of the sensor region is configured to block energy transferred between the subject and a physiological sensor. In some embodiments, at least a portion of the sensor region is configured to guide energy transferred between the subject and a physiological sensor. For example, the sensor region may include a lens that is configured to focus light transferred between the subject and a physiological sensor.

In some embodiments of the present invention, a monitoring apparatus housing may have a plurality of sensor regions, each configured to contact a respective selected area of the body of a subject when the housing is attached to the body of the subject. Each sensor region is contoured (i.e., "form-fitted") to matingly engage a respective selected body area. One or more physiological sensors may be associated with each sensor region and configured to detect and/or measure physiological information from the subject. In some embodiments, at least one sensor region of a monitoring apparatus has one or more sensors associated therewith that are configured to measure motion of the subject. Sensors for measuring motion may include, but are not limited to, sensors that measure changes in one or more of the following: inertia, capacitance, electrical conductivity, inductance, speed, distance, acceleration, and electromagnetic radiation.

In some embodiments, a sensor region of a monitoring apparatus may include a cover that is detachably secured to the sensor region. In some embodiments, the cover may be configured to regulate energy transferred between the subject and the physiological sensor. For example, the cover may be configured to block or filter certain types of energy.

According to some embodiments of the present invention, a monitoring apparatus includes a housing that is configured to be attached to a body of a subject, a physiological sensor supported by the housing and configured to detect and/or measure physiological information from the subject, and a plurality of interchangeable articles, each configured to be removably secured to the housing one at a time and each having a respective different shape. Each article is adapted to contact a selected body area when the housing is attached to the body of the subject, and the physiological sensor detects and/or measures physiological information from the subject via each article when removably secured to the housing. In some embodiments, each article is contoured to matingly engage the selected body area. The contour of each article may stabilize the housing when the housing is attached to the body of the subject. In some embodiments, each interchangeable article may include one or more physiological and/or environmental sensors.

According to some embodiments of the present invention, an earbud for a headset includes a housing that is configured to be positioned within an ear of a subject. The housing includes a sensor region that is configured to contact a selected area of the ear when the housing is attached to the ear of the subject. At least one physiological sensor is associated with the sensor region that detects and/or measures physiological information from the subject and/or at least one environmental sensor is associated with the sensor region and is configured to detect and/or measure environmental information. The sensor region is contoured to matingly engage the selected ear area and to stabilize the physiological and/or environmental sensor(s) relative to the selected ear area. In some embodiments, the sensor region contour stabilizes the housing when the housing is attached to the ear of the subject.

The sensor region of a monitoring apparatus, according to some embodiments of the present invention, can have various characteristics. For example, in some embodiments, at least a portion of a sensor region is detachable from the housing of the apparatus. In some embodiments, at least a portion of a sensor region is configured to block energy transferred between the subject and a physiological sensor. In some embodiments, at least a portion of a sensor region is configured to guide energy transferred between the subject and a physiological sensor. For example, a sensor region may include a lens that is configured to focus light transferred between the subject and a physiological sensor.

In some embodiments of the present invention, an earbud housing may have a plurality of sensor regions, each configured to contact a respective selected area of the ear of a subject when the housing is attached to the ear of the subject. Each sensor region is contoured (i.e., "form-fitted") to matingly engage a respective selected ear area. One or more physiological sensors may be associated with each sensor region and configured to detect and/or measure physiological information from the subject. In some embodiments, at least one sensor region of an earbud has one or more sensors associated therewith that are configured to measure motion of the subject. Sensors for measuring motion may include, but are not limited to, sensors that measure changes in one or more of the following: inertia, capacitance, electrical conductivity, inductance, speed, distance, acceleration, and electromagnetic radiation.

In some embodiments, a sensor region of an earbud may include a cover that is detachably secured to the sensor region. In some embodiments, the cover may be configured to regulate energy transferred between a subject and the physiological sensor. For example, the cover may be configured to block or filter certain types of energy.

Monitoring apparatus, according to the various embodiments of the present invention, may be utilized with mono headsets (i.e., headsets having one earbud) as well as stereo headsets (i.e., headsets having two earbuds). Moreover, earbuds according to the various embodiments of the present invention may be utilized with hearing aids, body jewelry, or any other attachment that can be placed near the head region, such as eye glasses or shades, a headband, a cap, helmet, face mask, visor, or the like.

BRIEF DESCRIPTION OF THE DRAWINGS

The accompanying drawings, which form a part of the specification, illustrate various embodiments of the present invention. The drawings and description together serve to fully explain embodiments of the present invention.

FIG. 9A is a rear plan view of an earbud module, according to some embodiments of the present invention.

FIG. 9B is a front plan view of the earbud module of FIG. 9A.

FIG. 9C is an exploded side view of the earbud module of FIG. 9A and a headset to which the earbud module is movably secured.

FIG. 10A is a side view of a headset and earbud module, according to some embodiments of the present invention.

FIG. 10B is cross-sectional view of an earbud module for the headset of FIG. 10A with a cover, according to some embodiments of the present invention.

FIG. 10C is cross-sectional view of an earbud module for the headset of FIG. 10A with a cover, according to some embodiments of the present invention.

DETAILED DESCRIPTION

Figure 1:
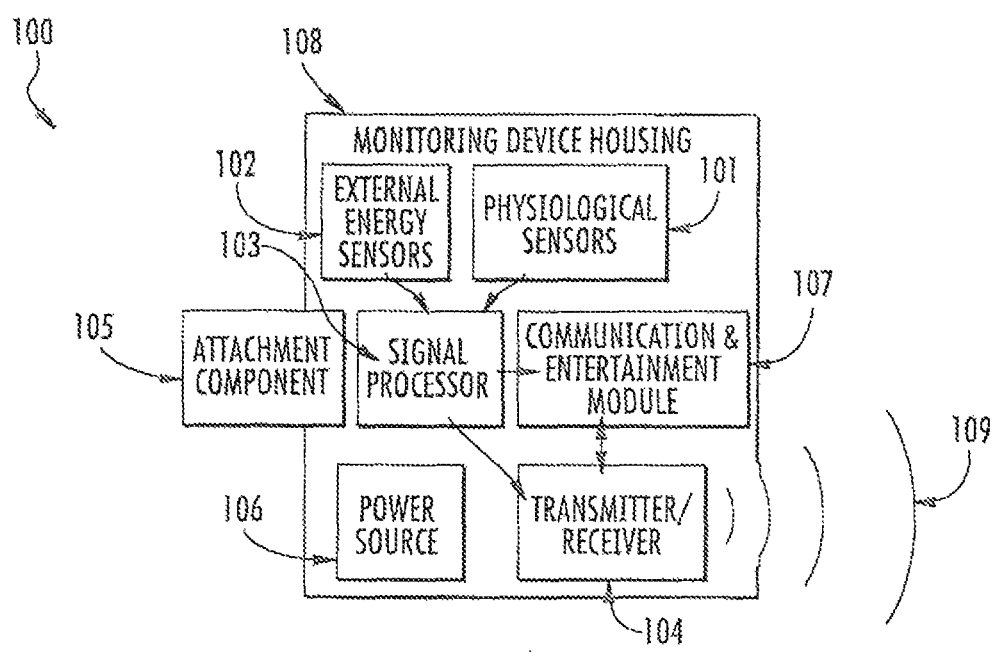
FIG. 1 is a block diagram of a monitoring device for physiological and environmental monitoring, according to some embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various features/elements, these features/elements should not be limited by these terms. These terms are only used to distinguish one feature/element from another feature/element. Thus, a first feature/element discussed below could be termed a second feature/element, and similarly, a second feature/element discussed below could be termed a first feature/element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "headset" includes any type of device or earpiece that may be attached to or near the ear (or ears) of a user and may have various configurations, without limitation. Headsets incorporating "form-fitted" sensor regions, as described herein, may include mono headsets (one earbud) and stereo headsets (two earbuds).

The term "real-time" is used to describe a process of sensing, processing, or transmitting information in a time frame which is equal to or shorter than the minimum timescale at which the information is needed. For example, the real-time monitoring of pulse rate may result in a single average pulse-rate measurement every minute, averaged over 30 seconds, because an instantaneous pulse rate is often useless to the end user. Typically, averaged physiological and environmental information is more relevant than instantaneous changes. Thus, in the context of the present invention, signals may sometimes be processed over several seconds, or even minutes, in order to generate a "real-time" response.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" includes monitoring blood gas levels, blood hydration, and metabolite/electrolyte levels.

The term "physiological" refers to matter or energy of or from the body of a subject (e.g., humans, animals, etc.). In embodiments of the present invention, the term "physiological" is intended to be used broadly, covering both physical and psychological matter and energy of or from the body of a creature. However, in some cases, the term "psychological" is called-out separately to emphasize aspects of physiology that are more closely tied to conscious or subconscious brain activity rather than the activity of other organs, tissues, or cells.

The term "body" refers to the body of a subject (human or animal) that may wear a form-fitted monitoring apparatus, according to embodiments of the present invention.

According to some embodiments of the present invention, monitoring apparatus containing one or more physiological and/or environmental monitors or sensors that have a shape or configuration that is form-fitted to a portion of the body of a subject are provided. The term "form-fitted" means that a monitoring apparatus, or one or more portions thereof, has a specific shape or configuration for mating engagement with a specific portion of the anatomy of a subject. This mating engagement provides stability that enhances monitoring efforts by the sensors associated therewith.

The ear is an ideal location for wearable health and environmental monitors. The ear is a relatively immobile platform that does not obstruct a person's movement or vision. Headsets located at an ear have, for example, access to the inner-ear canal and tympanic membrane (for measuring core body temperature), muscle tissue (for monitoring muscle tension), the pinna and earlobe (for monitoring blood gas levels), the region behind the ear (for measuring skin temperature and galvanic skin response), and the internal carotid artery (for measuring cardiopulmonary functioning), etc. The ear is also at or near the point of exposure to: environmental breathable toxicants of interest (volatile organic compounds, pollution, etc.); noise pollution experienced by the ear; and lighting conditions for the eye. Furthermore, as the ear canal is naturally designed for transmitting acoustical energy, the ear provides a good location for monitoring internal sounds, such as heartbeat, breathing rate, and mouth motion.

According to some embodiments of the present invention, monitoring apparatus with form-fitted portions for attachment to or near the ear of in a subject include various types of headsets, including wired or wireless headsets. Bluetooth®-enabled and/or other personal communication headsets may be configured to incorporate physiological and/or environmental sensors, according to some embodiments of the present invention. Bluetooth® headsets are typically lightweight, unobtrusive devices that have become widely accepted socially. Moreover, Bluetooth® headsets may be cost effective, easy to use, and are often worn by users for most of their waking hours while attending or waiting for cell phone calls. Bluetooth® headsets configured according to embodiments of the present invention are advantageous because they provide a function for the user beyond health monitoring, such as personal communication and multimedia applications, thereby encouraging user compliance with monitoring. Exemplary physiological and environmental sensors that may be incorporated into a Bluetooth® or other type of headsets include, but are not limited to accelerometers, acoustic sensors, auscultatory sensors, pressure sensors, humidity sensors, color sensors, light intensity sensors, pressure sensors, etc.

Headsets, both mono (single earbud) and stereo (dual earbuds), incorporating low-profile sensors and other electronics, according to embodiments of the present invention, offer a platform for performing near-real-time personal health and environmental monitoring in wearable, socially acceptable devices. The capability to unobtrusively monitor an individual's physiology and/or environment, combined with improved user compliance, is expected to have significant impact on future planned health and environmental exposure studies. This is especially true for those that seek to link environmental stressors with personal stress level indicators. The large scale commercial availability of a low-cost headset device can enable cost-effective large scale studies. The combination of monitored data with user location via GPS data can make on-going geographic studies possible, including the tracking of infection over large geographic areas. The commercial application of the proposed platform encourages individual-driven health maintenance and promotes a healthier lifestyle through proper caloric intake and exercise.

Accordingly, some embodiments of the present invention combine a personal communications headset device with one or more physiological and/or environmental sensors. Embodiments of the present invention are not limited to headsets that communicate wirelessly. In some embodiments of the present invention, headsets configured to monitor an individual's physiology and/or environment may be wired to a device that stores and/or processes data. In some embodiments, this information may be stored on the headset itself.

Although some embodiments illustrated herein are devices, such as headsets, that are configured to be attached at or near the ear of a subject, it is understood that form-fitted monitoring apparatus according to embodiments of the present invention can be utilized in proximity to any portion of the body of a subject, such as the limbs, torso, head, etc. In the case of an apparatus configured to sense physiological and/or environmental information near the ear region of a subject, any part of such an earpiece/headset device may have a form-fitted configuration.

FIG. 1 is a block diagram illustrating an earpiece module 100 that may include a form-fitted portion for attachment at or near the ear of a subject, according to some embodiments of the present invention. The illustrated earpiece module 100 includes one or more of the following: at least one physiological sensor 101, at least one environmental sensor 102 (also referred to as an external energy sensor), at least one signal processor 103, at least one transmitter/receiver 104, at least one power source 106, at least one communication & entertainment module 107, at least one earpiece attachment component 105, and at least one housing 108. Though the health and environmental sensor functionality can be obtained without the communication and entertainment module 107, having this additional module may promote use of the earpiece module 100 by users. The illustrated earpiece module 100 is intended primarily for human use; however, the earpiece module 100 may also be configured for use with other animals having ears sufficient to support an earpiece, such as primates, canines, felines, cattle, and most other mammals.

Earpiece monitoring apparatus according to embodiments of the present invention are not limited to the illustrated configuration of FIG. 1. A monitoring apparatus according to embodiments of the present invention may have only one or more physiological sensors, only one or more environmental sensors, or a combination of one or more physiological and environmental sensors. In some embodiments, a monitoring apparatus may not have one or more of the following: an earpiece attachment component 105, a communication and entertainment module 107, a signal processor 103 or a transmitter/receiver 104.

A physiological sensor 101 can be any compact sensor for monitoring the physiological functioning of the body, such as, but not limited to, sensors for monitoring: heart rate, pulse rate, breathing rate, blood flow, $VO_2$, $VO_{2max}$, blood oxygen, blood constituent levels, blood glucose level, heartbeat signatures, cardio-pulmonary health, organ health, metabolism, electrolyte type and concentration, physical activity, caloric intake, caloric metabolism, metabolomics, physical and psychological stress levels and stress level indicators, physiological and psychological response to therapy, drug dosage and activity (drug dosimetry), physiological drug reactions, drug chemistry in the body, biochemistry, position & balance, body strain, neurological functioning, brain activity, brain waves, blood pressure, cranial pressure, hydration level, auscultatory information, auscultatory signals associated with pregnancy, physiological response to infection, skin and core body temperature, eye muscle movement, blood volume, inhaled and exhaled breath volume, physical exertion, exhaled breath physical and chemical composition, the presence, identity, and concentration of viruses & bacteria, foreign matter in the body, internal toxins, heavy metals in the body, anxiety, fertility, ovulation, sex hormones, psychological mood, sleep patterns, hunger & thirst, hormone type and concentration, cholesterol, lipids, blood panel, bone density, body fat density, muscle density, organ and body weight, reflex response, sexual arousal, mental and physical alertness, sleepiness, auscultatory information, response to external stimuli, swallowing volume, swallowing rate, sickness, voice characteristics, tone, pitch, and volume of the voice, vital signs, head tilt, allergic reactions, inflammation response, auto-immune response, mutagenic response, DNA, proteins, protein or lactate levels in the blood, body hydration, water content of the blood, pheromones, internal body sounds, digestive system functioning, cellular regeneration response, healing response, stem cell regeneration response, and the like. Vital signs can include pulse rate, breathing rate, blood pressure, pulse signature, body temperature, hydration level, skin temperature, and the like. A physiological sensor may include an impedance plethysmograph for measuring changes in volume within an organ or body (usually resulting from fluctuations in the amount of blood or air it contains). For example, the earpiece module 100 may include an impedance plethysmograph to monitor blood pressure in real-time.

An external energy sensor 102, serving primarily as an environmental sensor, can be any compact sensor for monitoring the external environment in the vicinity of the body, such as, but not limited to, sensors for monitoring: climate, humidity, temperature, pressure, barometric pressure, pollution, automobile exhaust, soot density, airborne particle density, airborne particle size, airborne particle shape, airborne particle identity, volatile organic chemicals (VOCs), hydrocarbons, polycyclic aromatic hydrocarbons (PAHs), carcinogens, toxins, electromagnetic energy (optical radiation, X-rays, gamma rays, microwave radiation, terahertz radiation, ultraviolet radiation, infrared radiation, radio waves, and the like), EMF energy, atomic energy (alpha particles, beta-particles, gamma rays, and the like), gravity, light properties (such as intensity, frequency, flicker, and phase), ozone, carbon monoxide, greenhouse gases, $CO_2$, nitrous oxide, sulfides, airborne pollution, foreign material in the air, biological particles (viruses, bacteria, and toxins), signatures from chemical weapons, wind, air turbulence, sound and acoustical energy (both human audible and inaudible), ultrasonic energy, noise pollution, human voices, animal sounds, diseases expelled from others, the exhaled breath and breath constituents of others, toxins from others, bacteria & viruses from others, pheromones from others, industrial and transportation sounds, allergens, animal hair, pollen, exhaust from engines, vapors & fumes, fuel, signatures for mineral deposits or oil deposits, snow, rain, thermal energy, hot surfaces, hot gases, solar energy, hail, ice, vibrations, traffic, the number of people in a vicinity of the user, the number of people encountered throughout the day, other earpiece module users in the vicinity of the earpiece module user, coughing and sneezing sounds from people in the vicinity of the user, loudness and pitch from those speaking in the vicinity of the user, and the like.

Because the illustrated earpiece module 100 is capable of measuring and transmitting sensor information in real-time over a duration of time, the physiological and environmental sensors 101, 102 can be used to sense the aforementioned parameters over time, enabling a time-dependent analysis of the user's health and environment as well as enabling a comparison between the user's health and environment. Combined with proximity or location detection, this allows an analysis for pinpointing the location where environmental stress and physical strain took place. The signal processor 103 provides a means of converting the digital or analog signals from the sensors 101, 102 into data that can be transmitted wirelessly by the transmitter 104. The signal processor 103 may be composed of, for example, signal conditioners, amplifiers, filters, digital-to-analog and analog-to-digital converters, digital encoders, modulators, mixers, multiplexers, transistors, various switches, microprocessors, or the like. For personal communication, the signal processor 103 processes signals received by the receiver 104 into signals that can be heard or viewed by the user. The received signals may also contain protocol information for linking various telemetric modules together, and this protocol information can also be processed by the signal processor 103. The signal processor 103 may utilize one or more "compression/decompression" algorithms used in digital media (CODECs) for processing data. The transmitter/receiver 104 can be comprised of a variety of compact electromagnetic transmitters. A standard compact antenna is used in the standard Bluetooth headset protocol, but any kind of electromagnetic antenna suitable for transmitting at human-safe electromagnetic frequencies may be utilized. The transmitter/receiver 104 can also be an antenna. In some embodiments, the receiving antenna and the transmitting antenna are physically the same. The receiver/transmitter 104 can be, for example, a non-line-of-sight (NLOS) optical scatter transmission system. These systems typically use short-wave (blue or UV) optical radiation or "solar blind" (deep-UV) radiation in order to promote optical scatter, but IR wavelengths can also suffice. Additionally, a sonic or ultrasonic transmitter can be used as the receiver/transmitter 104 of the earpiece module 100, but preferably using sounds that are higher or lower than the human hearing range. A variety of sonic and ultrasonic receivers and transmitters are available in the marketplace and may be utilized in accordance with embodiments of the present invention.

In some embodiments, the transmitter/receiver 104 is configured to transmit signals from a signal processor 103 to a remote terminal following a predetermined time interval. For example, the transmitter/receiver 104 may delay transmission until a certain amount of detection time has elapsed, until a certain amount of processing time has elapsed, etc.

The power source 106 can be any portable power source capable of fitting inside the earpiece module housing 108. According to some embodiments, the power source 106 is a portable rechargeable lithium-polymer or zinc-air battery. Additionally, portable energy-harvesting power sources can be integrated into the earpiece module 100 and can serve as a primary or secondary power source. For example, a solar cell module can be integrated into the earpiece module 100 for collecting and storing solar energy. Additionally, piezoelectric devices or microelectromechanical systems (MEMS) can be used to collect and store energy from body movements, electromagnetic energy, and other forms of energy in the environment or from the user himself. A thermoelectric or thermovoltaic device can be used to supply some degree of power from thermal energy or temperature gradients. In some embodiments, a cranking or winding mechanism can be used to store mechanical energy for electrical conversion or to convert mechanical energy into electrical energy that can be used immediately or stored for later.

The various components describe above are configured to fit within the earpiece housing 108 and/or be attached thereto. The earpiece housing 108 may be formed from any safe and comfortable solid material, such as metal, rubber, wood, polymers, ceramic, organic materials, or various forms of plastic. The earpiece attachment component 105 is attached to the earpiece housing 108 and is designed to fit around or near the ear. For example, the standard Bluetooth headset includes an earpiece attachment that is connected to the headset housing via a double-jointed socket, to provide comfort and positioning flexibility for the user. In some embodiments, the earpiece attachment component 105 can be part of the housing 108, such that the entire earpiece module is one largely inflexible, rigid unit. In such case, a counterweight may be incorporated into the earpiece module 100 to balance the weight of the earpiece electronics and power source. In some embodiments, the earpiece attachment component 105 can contain physiological and environmental sensors, and the earpiece attachment component 105 may be detachable. In some embodiments, more than one earpiece attachment 105 can be attached to the earpiece module housing 108.

Figure 2:
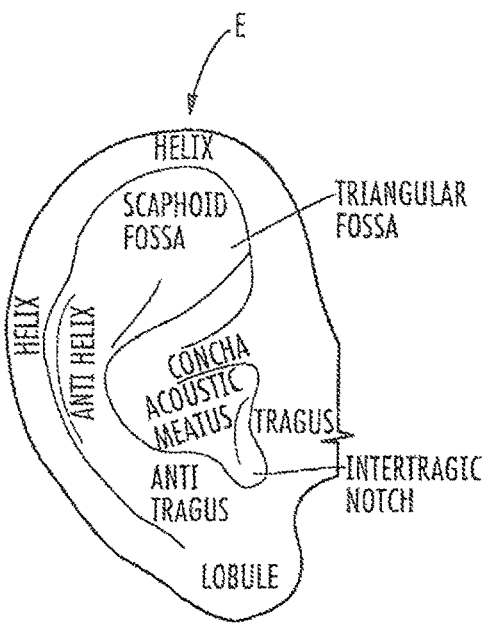
FIG. 2 illustrates the anatomy of a human ear.

FIG. 2 illustrates relevant anatomy of a human ear E. The anti tragus region is a particularly motion insensitive region for measuring physiological information from the ear during normal life activities. In contrast, a number of ear regions are particularly motion sensitive. For example, the ear canal, tragus, concha, helix, triangular fossa, intertragic notch, and neighboring regions may be particularly motion sensitive regions, especially when a person speaks, jogs, runs, etc. Placing sensors at these regions can be useful for generating signals that are entirely or mostly associated with motion only, with little (if any) signals associated with physiological information, or with contributions from both motion and physiological information. These signals can then be combined to generate a signal more closely associated with physiological information.

Figure 3:
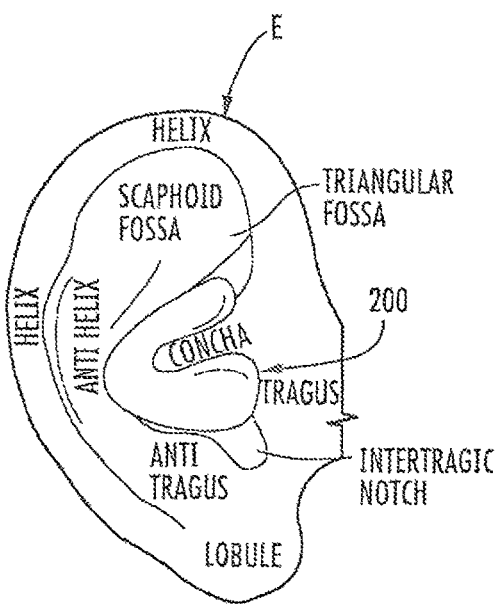
FIG. 3 illustrates a human ear with an earbud module attached thereto, according to some embodiments of the present invention.

FIG. 3 illustrates a monitoring apparatus 200, according to some embodiments of the present invention, attached to a human ear E. The monitoring apparatus 200 is an earbud module and is illustrated and described in more detail with respect to FIGS. 4A-4D.

Figure 4A:
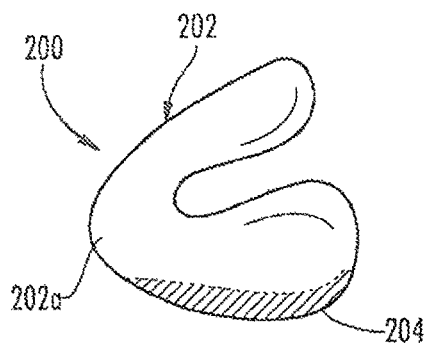
FIG. 4A is a front plan view of the earbud module of FIG. 3.
Figure 4B:
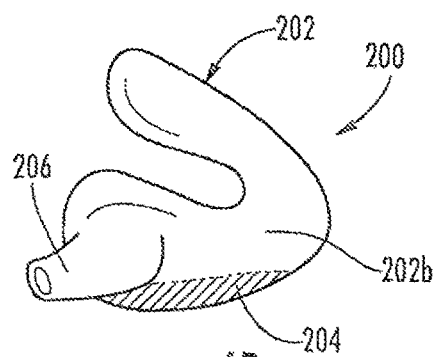
FIG. 4B is a rear plan view of the earbud module of FIG. 4A.
Figure 4C:
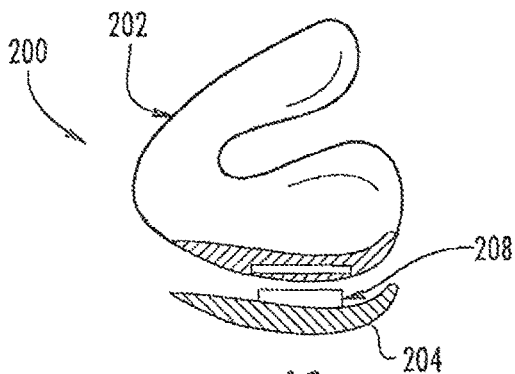
FIG. 4C is an exploded view of the earbud module of FIG. 4A with a detachable sensor region detached from the earbud housing, according to some embodiments of the present invention.

The illustrated monitoring apparatus 200 of FIG. 4A includes a housing 202 that is configured to be attached to the ear E of a subject, and that has a sensor region 204 that is configured to contact a selected area, of the ear E when the housing 202 is attached to the ear E. The sensor region 204 is contoured (i.e., is "form-fitted") to matingly engage a portion of the ear E between the anti tragus and acoustic meatus. As known to those skilled in the art, the region of the ear E between the anti tragus and the acoustic meatus contains a network of blood vessels that contain physiological information. Applicants have unexpectedly discovered that the this region of the ear E is resistant to motion artifacts. The housing 202 has a front or outer surface 202a and a rear or inner surface 202b. An elongated, hollow tube 206 extends outwardly from the housing rear surface 202b, as illustrated, and is configured to be inserted within the ear canal of an ear E.

In the illustrated embodiment, the sensor region 204 may be removable and may be replaced with a sensor region having a different contour. In other embodiments, the sensor region may be a fixed portion of the apparatus 200. Because the shape of the region of an ear E between the anti tragus and the acoustic meatus may vary from subject to subject, a sensor region 204 can be selected that has a contour that best aligns with the contour of any given subjects ear. The illustrated sensor region 204 is removably secured to the housing 202 via a connector 208 (FIG. 4C) which is configured to allow ready removal and attachment from/to the housing 202. Various types of connectors may be utilized without limitation, and embodiments of the present invention are not limited to any particular type of connector.

Figure 4D:
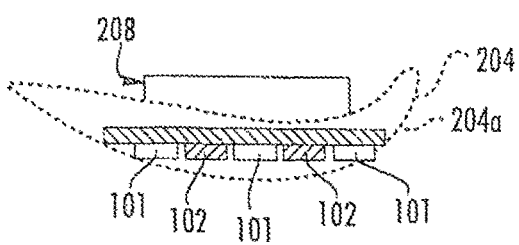
FIG. 4D is an enlarged plan view of the detachable sensor region of FIG. 4C.

As illustrated in FIG. 4D, the removable sensor region 204 contains physiological sensors 101 and environmental sensors 102, as described above. The physiological sensors 101 detect and/or measure physiological information from the subject and the environmental sensors 102 detect and/or measure environmental information, such as the ambient environment surrounding the person, environmental exposures by the person, environmental energy reaching the person, or the like. However, embodiments of the present invention are not limited to the illustrated removable sensor region with three physiological sensors 101 and two environmental sensors 102. As described above, one or more physiological sensors and/or one or more environmental sensors may be utilized. In some embodiments, one or more of the sensors 101, 102 may be configured to measure motion of a subject. Sensors for measuring motion may include, but are not limited to, sensors that measure changes in one or more of the following: inertia, capacitance, electrical conductivity, inductance, speed, distance, acceleration, and electromagnetic radiation.

In the illustrated embodiment, the sensors 101, 102 are embedded within the sensor region 204. The connector 208 may provide electrical contact between the sensors 101, 102 and another component(s) within the housing 202, such as a processor (103, FIG. 1), transmitter/receiver (104, FIG. 1), etc. In other embodiments, one or more of the sensors 101, 102 may be positioned on the surface 204a of the sensor region 204, or may be located at another region of the housing 202 in proximity to the sensor region 204.

Sensors 101, 102 utilized in or relative to sensor regions 204, according to embodiments of the present invention, are not limited to being in a planar configuration relative to each other. Sensors 101, 102 may be arranged in virtually any configuration on, within, and/or relative to a sensor region 204. In some embodiments two or more sensors 101, 102 may be arranged at angles to each other. In some embodiments, one or more sensors 101, 102 may be exposed via one or more openings or apertures in a sensor region 204. As a specific example, having an optical emitter and optical detector at, an angle from each other (such as a 45 degree angle) may be helpful in reducing unwanted optical scatter from being detected by the optical detector. In this way, the optical energy reaching, the optical detector may contain a greater ratio of physiological information with respect to optical scatter.

The sensor region contour stabilizes the physiological and/or environmental sensor(s) 101, 102 relative to the ear E such that subject motion does not negatively impact detection and/or measurement efforts of the sensor(s) 101, 102. In addition, the contour of the illustrated sensor region 204 stabilizes the housing 202 of the monitoring apparatus 200 when the housing 202 is attached to the ear E of a subject.

The sensor region 204 can have various characteristics. For example, in some embodiments, at least a portion of the sensor region 204 may be configured to block energy transferred between the subject and a physiological sensor 101. In some embodiments, at least a portion of the sensor region 204 may be configured to guide energy transferred between the subject and a physiological sensor 101. For example, the sensor region 204 may include a lens that is configured to focus light transferred between the subject and a physiological sensor. In some embodiments, the sensor region 204 may include a cover (not shown) that is detachably secured to the sensor region 204. The cover may be configured to regulate energy transferred between the subject and a sensor 101, 102 via the sensor region 204. For example, the cover may be configured to block or filter certain types of energy. In some embodiments, the sensor region 204 may be configured to modulate energy transferred between a blocked region and one or more sensors. As a specific example, the sensor region 204 may contain a material or structure that moves in response to physical motion, thereby modulating energy between a blocked region and a sensor.

Figure 7A:
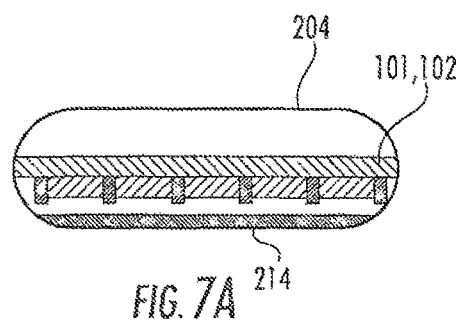
FIGS. 7A-7B are plan views of a sensor region for a monitoring apparatus, such as the earbud module of FIG. 6, according to some embodiments of the present invention.
Figure 7B:
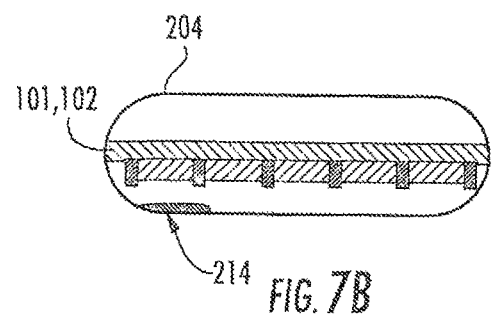
Figure 8A:
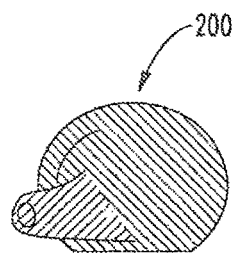
FIG. 8A is a front plan view of an earbud module, according to some embodiments of the present invention.
Figure 8B:
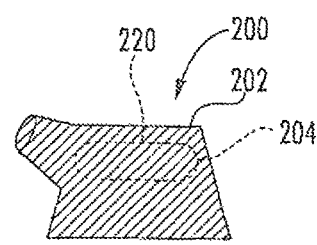
FIG. 8B is a bottom plan view of the earbud module of FIG. 8A.
Figure 8C:
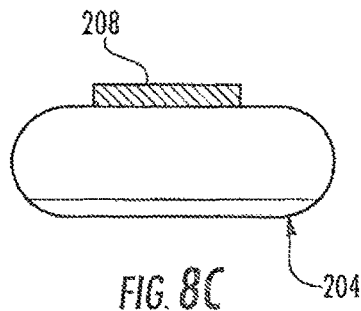
FIG. 8C is a front plan view of a detachable sensor region configured to be removably secured to the earbud module of FIG. 8A.
Figure 8D:
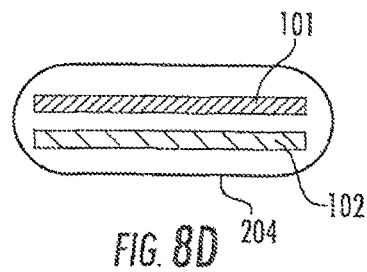
FIG. 8D is a bottom plan view of the detachable sensor region of FIG. 8C.

Referring now to FIGS. 7A-7B, a sensor region 204 for a monitoring apparatus 200, according to some embodiments of the present invention, is illustrated. The sensor region 204 may be a detachable sensor region as illustrated in FIGS. 4A-4D. The sensor region 204 may also be a non detachable portion of the housing of a monitoring device. The illustrated sensor region 204 includes at least one sensor (e.g., physiological sensor 101, environmental sensor 102) such as an optical sensor, embedded therewithin. The illustrated sensor region 204 also includes at least one energy regulating region 214 that that is configured to manipulate optical energy moving to and/or from a physiological region of interest. Examples of energy manipulation include, but or not limited to, blocking, guiding, concentrating, accelerating/decelerating, diffusing, focusing, frequency-converting, scattering, filtering, and reflecting the energy. In some embodiments, the energy regulating region 214 may be applied to all or a portion of a sensor 101, 102 (or to a portion of the sensor region 204). For example, as illustrated in FIG. 7A, the energy regulating region 214 blocks light entirely from the optical sensor 101, 102. In this embodiment, the structure of FIG. 7A may serve as a noise sensor (noise source) for sensing body motion. This structure may be located at several regions along the earbud or along other parts of the body to sense motion and provide motion noise information that can be subtracted from other physiological sensors to provide a signal that is at least partially removed of motion artifacts. In other embodiments, as illustrated in FIG. 7B, a portion of the optical sensor 101, 102 is blocked by the energy regulating region 214 such that the light cannot reach a physiological region of interest. In this way, light may pass from at least one optical emitting element of the sensor 101 to the energy regulating region 214 and scatter to be detected by at least one optical detecting element of the sensor 101, 102. In some embodiments where the sensor region 204 is not rigid, this scattered light can be indicative of motion artifacts. This scattered light can be compared with light scattering from a physiological region to extract the physiological signal from unwanted motion artifacts. Similarly, the scattered light from the energy regulating region 214 can provide information on motion without corruption from physiological information.

In another embodiment, the energy regulating region 214 may filter light of one or more particular wavelength ranges, such that only certain wavelengths reach the skin. For example, if the energy regulating region incorporates an optical filter for passing only IR light to reach the skin, visible wavelengths emitted by one or more optical emitters will not reach the skin. In this way, visible wavelengths may be scattered and this scattering intensity may be indicative of physical motion. In contrast, the IR light scattering from the skin may have its intensity modulated by both physiological changes and motion-related changes. Thus, visible scattered light can be compared with IR light scattering from a physiological region to extract the physiological signal from unwanted motion artifacts. Similarly, the scattered light from the energy regulating region 214 can provide information on motion without corruption from physiological information.

Sensor 101, 102 in FIGS. 7A-7B need not be an optical sensor and the energy regulating region 214 need not be optical in nature. For example, sensor 101, 102 may be a capacitive sensor that can measure changes in electric field, where the electric field is selectively blocked by the energy regulating region 214 of sufficiently dissimilar permittivity or electrical conductivity region. Similarly, sensor 101, 102 may be an acoustic sensor that can measure changes in sound, where the sonic energy is selectively blocked by the energy regulating region 214 of dissimilar density. Similarly, the sensor 101, 102 may be a electrical conductivity sensor or electrode that can measure changes in electrical conductivity, where the electrical conductivity through the skin or body is selectively blocked by the energy regulating region 214 via an electrically insulating region. Similarly, the regulating region 214 may cover at least one emitter, detector, or combination of both. Similarly, sensor 101, 102 may be an optical sensor, and the energy regulating region 214 may include at least one mechanical structure, such as a flap, lever, membrane, or the like, for vibrating with physical motion. This vibration would modulate the optical energy in proportion to body motion. In some embodiments, the elements of FIGS. 7A-7B may be integrated into a microelectromechanical system (MEMS) device. In each case, changes in energy scatter from the energy regulating region 214 are predominantly associated with motion artifacts, whereas changes in energy scatter from the unregulated regions contains information on both physiological status and motion.

Monitoring apparatus and components thereof, according embodiments of the present invention, can be fabricated by standard manufacturing techniques, including, but not limited to, injection molding, forming, extrusion, coating, and the like. In some embodiments, a sensor region 204 may be molded over sensor elements 101, 102 to yield a tight fit between these components. For optical sensors, the material composing the sensor region 204 is at least partially transparent to the relevant optical wavelengths. An energy regulating region 214 may be coated onto the surface 204a of a sensor region 204, incorporated into the material of the sensor region 204, or selectively deposited onto portions of the sensor region 204 or components thereof. Dielectric coatings and films may be utilized as coated energy regulating regions. For example, polyethylene film may be used to block UV light, and organic films and materials may be used to selectively pass light. For example, the materials in developed photographic film and certain dyes may pass IR light and reject other wavelengths. Similarly, Bragg reflector regions may be used to pass or reject certain wavelengths. In some embodiments, an energy regulating region 214 may be the same material as a sensor region 204. For example, optical-pass materials, such visible-pass, IR-pass plastics and UV-block plastics (such as polyethylene), may be suitable for regulating optical energy and may constitute at least part of the material used in a sensor region 204. In some embodiments, the material of a sensor region 204 may be doped and/or selectively doped with another material for regulating energy flow. Plastics and rubber as base materials may be ideal due to the soft, comfortable feel against the skin and the ability to form-fit these materials under compression.

Figure 11A:
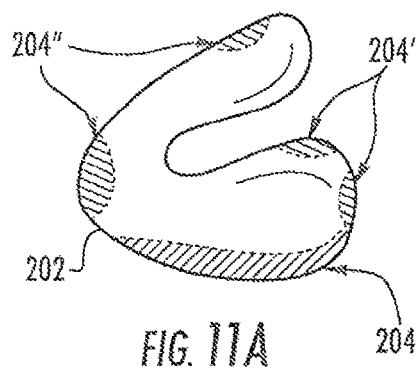
FIG. 11A is a rear plan view of an earbud module, according to some embodiments of the present invention.
Figure 11B:
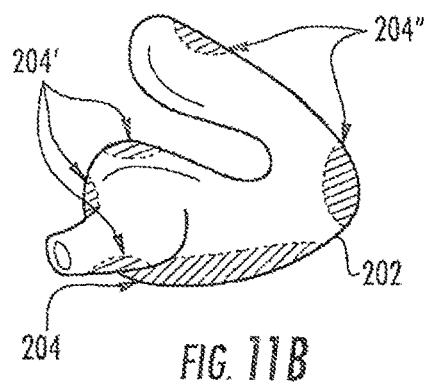
FIG. 11B is a front plan view of the earbud module of FIG. 11A.

In some embodiments of the present invention, a monitoring apparatus housing may have a plurality of sensor regions, each configured to contact a respective selected area of the body of the subject when the housing is attached to the body of the subject. Each sensor region may be contoured (i.e., "form-fitted") to matingly engage a respective selected body area. One or more physiological sensors 101 may be associated with each respective sensor region and configured to detect and/or measure physiological information from the subject. For example, as illustrated in FIGS. 11A-11B, the monitoring apparatus 200 of FIG. 4A may have a plurality of sensor regions 204, each configured to contact a respective selected area of the ear E of a subject when the housing 202 is attached to the ear. Each sensor region is contoured (i.e., "form-fitted") to matingly engage a respective selected ear region.

Figure 5A:
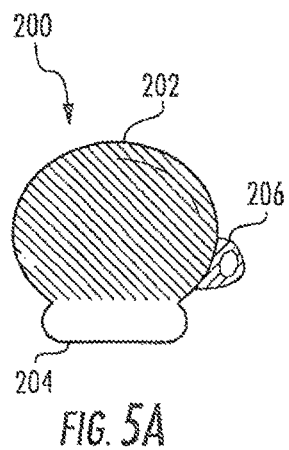
FIG. 5A is a rear plan view of an earbud module, according to some embodiments of the present invention.
Figure 5B:
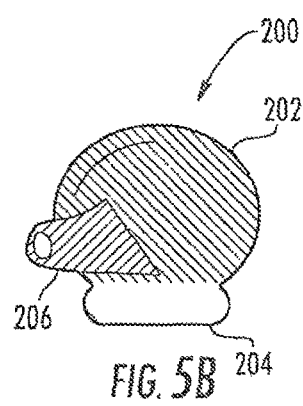
FIG. 5B is a front plan view of the earbud module of FIG. 5A.
Figure 5C:
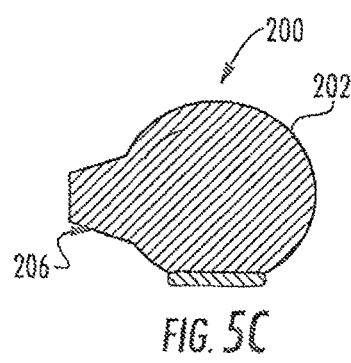
FIG. 5C is a front plan view of an earbud module, according to some embodiments of the present invention.

FIGS. 5A-5C illustrate a monitoring apparatus 200 in the form of an earbud module, according to other embodiments of the present invention. The illustrated apparatus 200 is essentially identical to the monitoring apparatus 200 of FIG. 4A except for the shape of the housing 202, which has a different configuration and which includes a sensor region 204 that is more bulbous than the sensor region 204 of FIG. 4A. The bulbous sensor region 204 is configured to fit snuggly between the anti tragus and acoustic meatus of a human ear. Because human ears have different shapes, different geometries of the sensor region 204 may be necessary for stabilizing the housing 202 within an ear E. For example, the sensor region 204 of FIG. 5C is smaller in size than the sensor region 204 depicted in FIG. 5B.

Figure 6:
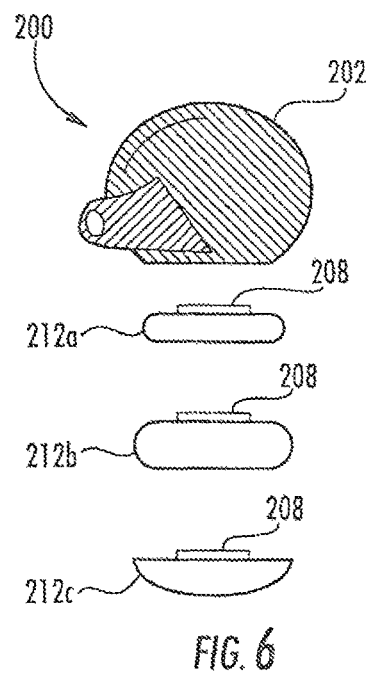
FIG. 6 is a an exploded view of an earbud module and a plurality of interchangeable articles configured to be removably secured to the earbud module, according to some embodiments of the present invention.

FIG. 6 illustrates a monitoring apparatus 200 according to some embodiments of the present invention having a housing 202 that is configured to be attached to the ear of a subject and that includes a plurality of interchangeable articles 212a-212c, each configured to be removably secured to the housing one at a time and each having a respective different shape. Each article 212a-212c is adapted to contact a selected ear area. One of the articles 212a-212c is selected depending on the shape of an ear in which the housing 202 is to be attached. For example, larger ears may require a larger article 212b, and curvier ears may require a curvier article 212c.

In some embodiments, these interchangeable articles 212a-212c may be sensor regions 204, as described above. In other embodiments, these interchangeable articles 212a-212c may be used only to provide stability to the housing 202 when attached to an ear. When used as sensor regions, each article 212a-212c may have various characteristics (e.g., block or filter certain types of energy, focus light, etc.) as described above. In addition, each article 212a-212c may include one or more physiological and/or environmental sensors.

Referring now to FIGS. 8A-8D, a monitoring apparatus 200, according to other embodiments of the present invention is illustrated. The illustrated monitoring apparatus 200 is an earbud module with a housing 202 having a portion 220 configured to removably receive a detachable sensor region 204 therein via connector 208. The sensor region 204 may contain one or more physiological sensors and/or one or more environmental sensors. In the illustrated embodiment, the sensor region 204 includes a physiological sensor 101 and an environmental sensor 102. These sensors may be spread out throughout the length of the sensor region 204 to provide a wider angle of sensor area such that motion artifacts have less of an impact on physiological sensing. In some embodiments, at least one sensor 101, 102 may be an optical sensor with a diffuse optical emitter. OLEDs and phosphor-coated LED sources are examples of diffuse optical emitters.

Referring to FIGS. 9A-9C, a monitoring apparatus 200, according to other embodiments of the present invention, is illustrated. The illustrated monitoring apparatus 200 is an earbud module with a housing 202 that is configured to be rotatably secured to a headset 300. The headset 300 includes a projecting portion 302 extending outwardly, as illustrated in FIG. 9C. This projecting portion 302 is configured to be inserted within a cavity 203 in the earpiece housing 202. This configuration allows the earbud module housing 202 and headset housing 300 to rotate relative to each other about axis $A_1$. Rotation may be needed to adjust the position of a microphone within the headset 300 relative to a mouth of a user. In the illustrated embodiment, an electrical connector 212 is shown and that extends from one or more sensors 101, 102 in the sensor region 204 through the projecting portion 302 for connecting the one or more sensors 101, 102 to a processor 103 or other component(s) in the headset housing 300.

The illustrated earbud module housing 202 includes a bulbous sensor region 204, similar to that described and illustrated in FIGS. 5A-5B. The bulbous sensor region 204 is configured to fit snuggly between the anti tragus and acoustic meatus of a human ear. The bulbous configuration of sensor region 204 allows the sensor region 204 to remain stable when the earbud module housing 202 and headset housing 300 rotate relative to each other about axis $A_1$. Stabilization provided by the sensor region 204 may be important because the swivel action may otherwise impart motion artifacts upon sensor(s) 101, 102 in the sensor region 204.

Referring to FIGS. 10A-10C, a monitoring apparatus, according to other embodiments of the present invention, is illustrated. The illustrated monitoring apparatus is a headset 300 with an earbud module 200 and an ear hook 105 for securing the headset 300 to the ear of a user. Different sizes and shapes of ears may require different earbud sizes and shapes. For this reason, a detachable cover 230 is removably secured to the earbud module housing 202, as shown in FIGS. 10B-10C. Detachable covers of various sizes may be provided, according to embodiments of the present invention. As such an earbud module may be custom fit to a particular ear of a user by selecting a cover 230 having a shape that best matches the shape of a user ear.

Figure 12:
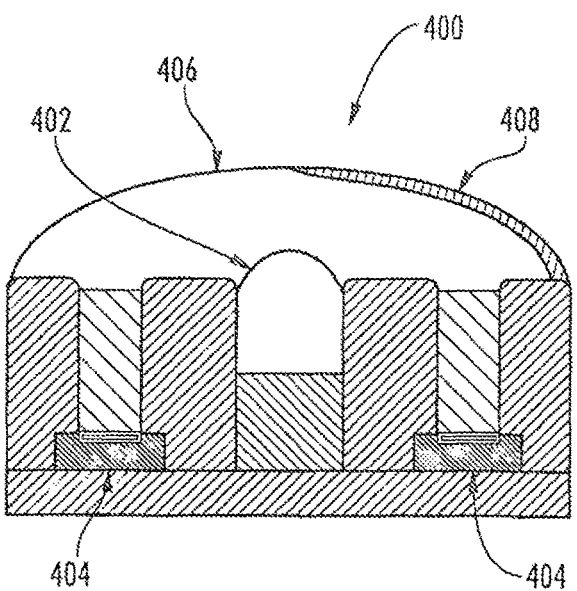
FIG. 12 is a cross-sectional view of an optical sensor module, according to some embodiments of the present invention.

Referring now to FIG. 12, an optical sensor module 400 that may be incorporated into a sensor region 204 of a monitoring apparatus, according to embodiments of the present invention, is illustrated. The illustrated optical sensor module 400 includes at least one optical emitter 402 and a plurality of optical detectors 404. Covering the optical emitter 402 and detectors 404 is at least one lens 406. The lens 405 includes an optical regulating region 408 that prevents at least one region of the optical sensor module 400 from receiving light scattered by physiological material. The optical regulating region 408 may be located at any region that prevents optical energy having physiological information from reaching at least one detector 404. In the illustrated embodiment, the optical regulating region 408 is at least partially reflective of light.

In other embodiments, the optical sensor module 400 may include more than one optical emitter 402 and at least one optical detector 404 to generate equal results, as long as the optical energy from the at least one optical emitter 402 is regulated by at least one energy regulating region 408. In some embodiments, the optical emitter 402 and detectors 404 may be isolated by an optical blocking material to prevent unwanted optical signals from triggering the optical detectors.

Referring to FIGS. 11A-11B, a monitoring apparatus 200 in the form of an earbud module includes a housing 202 that is configured to be attached to the ear E of a subject. The housing 202 includes multiple sensor regions 204, 204', 204" that are configured to contact respective selected areas of an ear E when the housing 202 is attached to the ear E. Each sensor region 204, 204', 204" is contoured to matingly engage a respective selected ear area. At least one physiological sensor and/or environmental sensor is associated with each sensor region that is configured to detect and/or measure physiological and/or environmental information from the subject. The use of multiple sensor regions 204, 204', 204" facilitates the extraction of motion artifacts from physiological sensor readings. In the illustrated embodiment, sensor region 204 includes sensors for detecting physiological and/or environmental information. Sensor regions 204' and/or 204" may be associated with sensors for detecting motion. For example, in some embodiments, signals detected at the motion sensor regions 204' may be used to detect speech to facilitate noise cancellation and/or sensor regions 204' may be used to detect generalized motion of the human body, such as motion during writing, clapping, walking, jogging, running, or the like. This description of sensor regions is not meant to limit the invention. A variety of spatial sensor configurations may be used to extract physiological information and reduce noise.

Figure 13A:
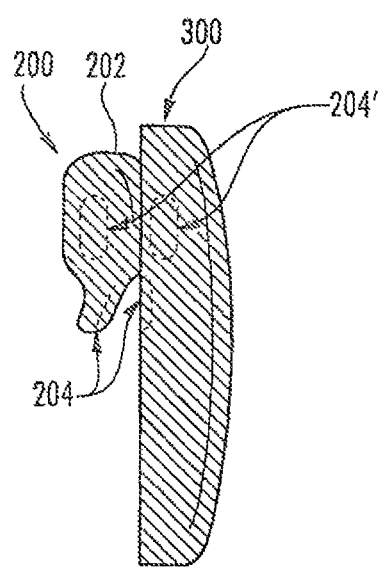
FIG. 13A is a side view of a headset having an earbud module, according to some embodiments of the present invention.
Figure 13B:
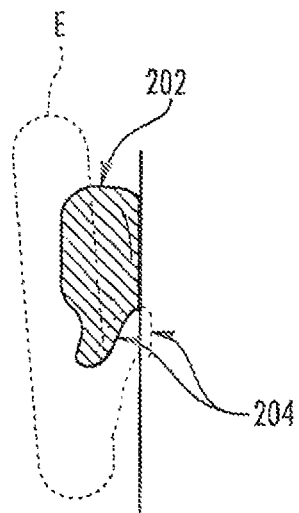
FIG. 13B illustrates the headset of FIG. 13A attached to an ear of a subject.

Monitoring apparatus, according to embodiments of the present invention, may include sensor regions associated with reflection-mode sensors and/or sensor regions associated with transmission-mode sensors. The term "reflection-mode" refers to a method of measuring physiological information with scattered excitation energy that has not fully penetrated a part of the body of a subject. The term "transmission-mode" refers to a method of measuring physiological information with scattered excitation energy that has fully penetrated at least one part of the body of a subject. FIGS. 13A-13B illustrate a transmission-mode earbud module 200. The earbud module 200 is attached to a headset 300. A pair of sensor regions 204 are in adjacent, spaced-apart relationship, as illustrated, with one sensor region 204 on the earbud module 200 and the other sensor region 204 on the headset 300. These sensor regions 204 are configured to pass energy from one to the other when the tragus region of an ear E of a subject is positioned between these sensor regions. In the illustrated embodiment, the earbud module 200 and headset 300 also include sensor regions 204' in adjacent, spaced-apart relationship. In this configuration, the anti tragus can be positioned between the two sensor regions 204' for emitting and detecting energy.

Figure 14A:
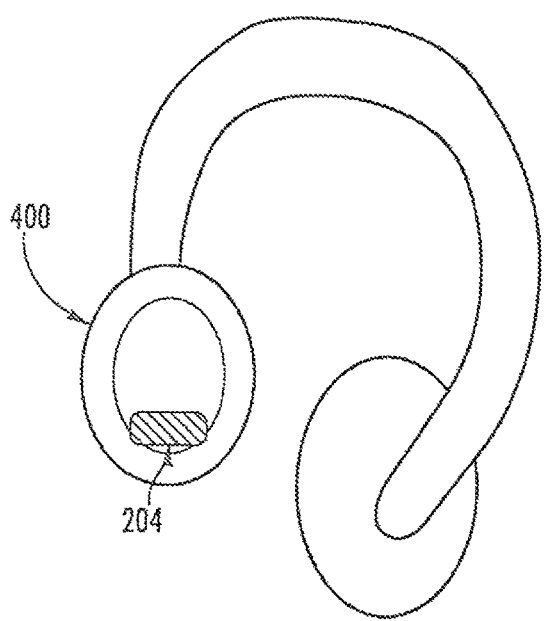
FIG. 14A is a perspective view of a headset with earmuffs and wherein an earmuff thereof includes a sensor region, according to some embodiments of the present invention.
Figure 14B:
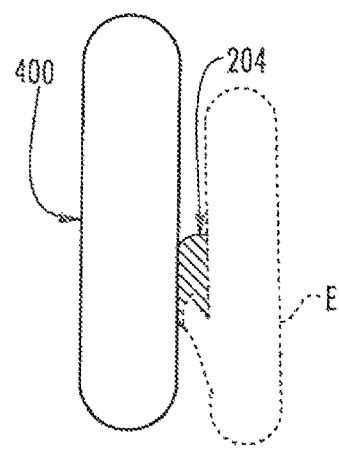
FIG. 14B illustrates the headset of FIG. 14A attached to an ear of a subject.

Embodiments of the present invention may be utilized in form-factors other than traditional earbud designs. FIGS. 14A-14B illustrate a sensor so region in an earmuff 400, where the sensor region 204 is part of the earmuff form-factor. The sensor region 204 is located in the earmuff 400 such that the sensor region 204 is in proximity to at least one region of the ear E of a subject.

Health and environmental monitors, according to, embodiments of the present invention, enable low-cost, real-time personal health and environmental exposure assessment monitoring of various health factors. An individual's health and environmental exposure record can be provided throughout the day, week, month, or the like. Moreover, because the health and environmental sensors can be small and compact, the overall size of an apparatus, such as an earpiece, can remain lightweight and compact.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A method of at least partially removing motion artifacts from physiological signals produced by a physiological sensor of a wearable device, wherein the physiological sensor includes at least one optical emitter and at least one optical detector, the method comprising:
   detecting light emitted by the at least one optical emitter that is scattered by a body of a subject wearing the wearable device and producing a physiological information signal therefrom via the at least one optical detector;
   detecting light emitted by the at least one optical emitter that is scattered by a light regulating region of the wearable device as a result of movement of the wearable device and producing a motion noise information signal via the at least one optical detector, wherein the light regulating region is configured to only allow light at one or more selected wavelengths from reaching the body of the subject; and
   processing the physiological information signal and the motion noise information signal via at least one processor associated with the wearable device to at least partially remove unwanted motion artifacts from the physiological information signal.

2. The method of claim 1, wherein the light scattered by the body of the subject and the light scattered by the light regulating region of the wearable device travel through separate first and second regions of the wearable device.

3. The method of claim 2, wherein the first region of the wearable device is configured to guide light between the sensor and the body of the subject.

4. The method of claim 1, wherein the light regulating region of the wearable device is configured to at least partially block light from the at least one optical emitter from reaching the body of the subject.

5. The method of claim 1, wherein the light regulating region of the wearable device comprises an optical filter configured to allow infrared light to pass therethrough.

6. The method of claim 1, wherein the light regulating region of the wearable device comprises an optical filter configured to block light at visible wavelengths from passing therethrough.

7. The method of claim 1, wherein the light regulating region of the wearable device comprises one of a flap, lever, or membrane that moves in response to subject motion.

8. The method of claim 1, wherein the light regulating region of the wearable device moves in response to subject motion.

9. The method of claim 1, wherein the light regulating region of the wearable device comprises an optically reflecting material.

10. The method of claim 1, wherein processing the physiological information signal and the motion noise information signal comprises subtracting the motion noise information signal from the physiological information signal.

11. The method of claim 1, wherein the steps of detecting light emitted by the at least one optical emitter that is scattered by the body of the subject and detecting light emitted by the at least one optical emitter that is scattered by the light regulating region of the wearable device are performed substantially simultaneously.

12. A motion noise sensor configured to be attached to a body of a subject, the motion noise sensor comprising:
- at least one optical emitter;
- at least one optical detector; and
- a light regulating region configured to only allow light from the at least one optical emitter at one or more selected wavelengths from reaching the body of the subject, wherein the light regulating region is configured to move in response to subject motion;
- wherein the at least one optical detector is configured to detect light scattered by the light regulating region.

13. The motion noise sensor of claim 12, wherein the light regulating region comprises one of a flap, lever, or membrane that moves in response to subject motion.

14. The motion noise sensor of claim 12, wherein the light regulating region comprises an optical filter configured to allow infrared light to pass therethrough.

15. The motion noise sensor of claim 12, wherein the light regulating region comprises an optical filter configured to block light at visible wavelengths from passing therethrough.

16. A wearable apparatus, comprising:
- a physiological sensor comprising at least one optical emitter and at least one optical detector; and
- a light regulating region configured to only allow light at one or more selected wavelengths from reaching the body of the subject,
- wherein the at least one optical detector is configured to detect light from the at least one optical emitter that is scattered by a body of a subject wearing the wearable apparatus and to produce a physiological information signal therefrom, and
- wherein the at least one optical detector is configured to detect light from the at least one optical emitter that is scattered by the light regulating region as a result of movement of the wearable apparatus and to produce a motion noise information signal therefrom.

17. The wearable apparatus of claim 16, wherein the at least one optical detector comprises at least two optical detectors.

18. The wearable apparatus of claim 16, further comprising at least one processor configured to process the physiological information signal and the motion noise information signal to at least partially remove unwanted motion artifacts from the physiological information signal.

19. The wearable apparatus of claim 16, wherein the light regulating region is configured to move in response to subject motion.

20. The wearable apparatus of claim 16, wherein the light regulating region comprises one of a flap, lever, or membrane that moves in response to subject motion.

21. The wearable apparatus of claim 16, wherein the light regulating region comprises an optical filter configured to allow infrared light to pass therethrough.

22. The wearable apparatus of claim 16, wherein the light regulating region comprises an optical filter configured to block light at visible wavelengths from passing therethrough.

23. The wearable apparatus of claim 16, wherein the wearable apparatus is an earbud configured to be positioned within an ear of the subject.

24. The wearable apparatus of claim 16, wherein the wearable apparatus is a headset configured to be attached at or near an ear of the subject.

25. The wearable apparatus of claim 16, wherein the wearable apparatus is configured to be attached to a limb, a nose, an earlobe, and/or a digit of the subject.

* * * * *

UNITED STATES PATENT AND TRADEMARK OFFICE
CERTIFICATE OF CORRECTION

PATENT NO. : 10,092,245 B2
APPLICATION NO. : 14/740804
DATED : October 9, 2018
INVENTOR(S) : LeBoeuf et al.

Page 1 of 1

It is certified that error appears in the above-identified patent and that said Letters Patent is hereby corrected as shown below:

On the Title Page

Page 6, Column 1, Item (56) References Cited, FOREIGN PATENT DOCUMENTS:
Please correct "WO 2005/03212" to read -- WO 2005/036212 --

In the Specification

Column 16, Line 64: Please correct "405" to read -- 406 --

Column 17, Line 17: Please correct "204" to read -- 204' -- (Second Occurrence)

Column 17, Line 20: Please correct "204" to read -- 204' -- (Second Occurrence)

Column 17, Line 26: Please correct "204" to read -- 204' --

Column 17, Line 34: Please correct "204'" to read -- 204" --

Signed and Sealed this
Fifteenth Day of January, 2019

Andrei Iancu
*Director of the United States Patent and Trademark Office*